United States Patent [19]

Miyazaki et al.

[11] Patent Number: 5,679,581

[45] Date of Patent: *Oct. 21, 1997

[54] METHOD FOR MEASURING AN IMMUNOLOGICALLY ACTIVE MATERIAL AND APPARATUS SUITABLE FOR PRACTICING SAID METHOD

[75] Inventors: Takeshi Miyazaki, Ebina; Kazumi Tanaka, Yokohama; Masanori Sakuranaga, Atsugi; Tadashi Okamoto, Yokohama, all of Japan

[73] Assignee: Canon Kabushiki Kaisha, Tokyo, Japan

[ * ] Notice: The term of this patent shall not extend beyond the expiration date of Pat. No. 5,534,441.

[21] Appl. No.: 372,877

[22] Filed: Jan. 13, 1995

Related U.S. Application Data

[63] Continuation of Ser. No. 173,465, Dec. 27, 1993, abandoned, which is a continuation of Ser. No. 24,861, Feb. 26, 1993, abandoned, which is a continuation of Ser. No. 571,197, Aug. 23, 1990, abandoned.

[30] Foreign Application Priority Data

| Aug. 23, 1989 | [JP] | Japan | 1-214889 |
| Jul. 12, 1990 | [JP] | Japan | 2-184527 |
| Jul. 13, 1990 | [JP] | Japan | 2-185681 |

[51] Int. Cl.$^6$ ............................................. G01N 33/557
[52] U.S. Cl. .................. 436/517; 436/64; 436/65; 436/164; 436/518; 436/531; 436/533; 436/805; 436/813; 436/814
[58] Field of Search ............ 435/7.1, 7.4; 436/424, 436/510, 517, 518, 531, 533, 64, 65, 164, 805, 813, 814

[56] References Cited

U.S. PATENT DOCUMENTS

| 4,419,453 | 12/1983 | Dorman et al. | 436/534 |
| 4,829,012 | 5/1989 | Cambiaso et al. | 436/512 |

FOREIGN PATENT DOCUMENTS

| 52-117420 | 10/1977 | Japan . |
| 53-12966 | 5/1978 | Japan . |
| 53-52620 | 5/1978 | Japan . |
| 58-73866 | 5/1983 | Japan . |
| 62-46262 | 1/1987 | Japan . |

OTHER PUBLICATIONS

J. M. Singer et al., "The Latex Fixation Test," American Journal of Medicine, Dec. 1956, pp. 888–892.

A. Faure et al., "Quantitative Study of Tests Using Latex Particles Coated with Proteins or Peptides," Protides Biol. Fluids, Proc. Colloq., 2589 (1972), pp. 589–593.

Immobilization Enzymes, ed. Ichiro Chihata Kodansha (1975), pp. 10–43 (please see p. 16 of the specification where this reference is cited and discussed, no English translation was available).

Immunological Procedure VIII, Bunko-do 2401 (1979), pp. 2401–2411 (please see p. 26 of the specification where this reference is cited and discussed, no English translation was available).

Diagnostic Test 30, vol. 30, No. 11, pp. 1258–1265 (please see p. 30 of the specification where this reference is cited and discussed, no English translation was available).

Primary Examiner—Donald E. Adams
Assistant Examiner—Jeffrey Stucker
Attorney, Agent, or Firm—Fitzpatrick, Cella, Harper & Scinto

[57] ABSTRACT

There are provided a method and an apparatus for measuring an immunologically active material by physically or chemically immobilizing material immunologically active to a material to be measured of a specimen to the dehydrated solid fine particles, providing a desirable dispersion comprising said immunologically active material immobilized to said solid fine particles and said specimen in a liquid medium, reacting them to cause a reaction mixture in an agglutinated state and optically measuring said agglutinated state of the reaction mixture to thereby quantitatively determine the content of said material to be measured with an improved accuracy.

9 Claims, 8 Drawing Sheets

METHOD FOR MEASURING AN IMMUNOLOGICALLY ACTIVE MATERIAL AND APPARATUS SUITABLE FOR PRACTICING SAID METHOD

This application is a continuation of application Ser. No. 08/173,465, filed Dec. 27, 1993, now abandoned; which in turn is a continuation of application Ser. No. 08/024,861, filed Feb. 26, 1993, now abandoned; which in turn, is a continuation of application Ser. No. 07/571,197, filed Aug. 23, 1990, now abandoned.

FIELD OF THE INVENTION

The present invention relates to a method and an apparatus for measuring an immunologically active material such as antigen or antibody contained in a specimen with the use of dehydrated solid fine particles (hereinafter referred to as "dry solid fine particles"). More particularly, the present invention relates a method and an apparatus for optically measuring said immunologically active material wherein dry solid fine particles having an immunologically active material immobilized on their surfaces are used and the agglutination degree of a product resulted as a result of antigen-antibody reaction is optically measured.

BACKGROUND OF THE INVENTION

A latex agglutination immunoassay method (LAIA method) was developed by J. M. Singer et al [see, Am. J. Med., 21888 (1956)]. In the LAIA method, a dispersion (latex reagent) obtained by dispensing an immunologically active material such as antibody being disposed on fine particles of polystyrene in a liquid medium such as water is effected with a material having a selective reactivity such as antibody to said immunologically active material to cause an agglutinated body and the agglutinated state of the resultant is observed by eyes to thereby recognize the presence of the material to be observed. Since then, there have been made various studies on this method. Although quantitative determination is difficult, said method of recognizing the presence of an objective material by observing the agglutinated state of such agglutinated body by eyes has been widely used since the method is simple and provides a result for a short period of time.

In order to obtain a precise result, there was made an attempt to observe the agglutinated degree of the agglutinated body by an optically measuring means.

For instance, A. Fature et al proposed a method of optically observing a change in the turbidity caused by agglutination reaction and performing quantitative determination of an objective material based on the dynamic analysis [see, Protides Biol Fluids, Proc. Colloq., 2589 (1972)]. This method is however problematic that the values obtained will be greately varied because of unstableness of a latex reagent to be used and the method is not sufficient in the measuring sensitivity. More particularly with respect to the method of A. Fature et al., the latex reagent used is of a state that solid fine particles are dispersed in a liquid dispersing medium and it is substantially unstable. And there are problems for the latex reagent that it is likely to cause agglutination and/or reduction in its sensitivity upon storage for a long period of time, the dispersed state thereof will be destroyed upon cryopreservation and thus, specific due regards should be made upon its storage in order to prevent occurrence of these problems.

In order to eliminate the above problems of the latex reagent, there was made a proposal of freeze-drying the latex reagent comprising solid fine particles dispersed in a liquid dispersing medium to maintain its stability upon storage by Japanese Unexamined Patent Publication 52(1977)-117420 or 62(1987)-46262. According to this proposal, there is an advantage that the stability upon storage of the latex reagent is improved. However, there are still unsolved problems that a latex reagent obtained by redisperse the dried product in a liquid dispersing medium is not always constant in the agglutination reactivity and because of this, there is caused a variation for the resulting measured data.

In view of the above, according to such known method, it is possible to qualitatively detect the presence of an objective material contained in a specimen, but it is extremely difficult to quantitatively measure said material with a high accuracy.

Now, there is another proposal for detecting an immunologically active material contained in a specimen by injecting an agglutinated immune reagent such as latex reagent into a capillary tube, followed by freeze-drying, mixing the resultant with a specimen in said capillary tube, reacting them to cause an agglutinated body and observing the agglutinated state of said body (see, Japanese Unexamined Patent Publication 58(1983)-73866). This method is advantageous in the viewpoints that the reagent is stably maintained upon storage and the procedures are simple. However, this method is still problematic that the reproducibility of a measured value is not sufficient and it is difficult to perform precise quantitative determination of an objective material contained in a specimen.

SUMMARY OF THE INVENTION

The present invention makes it an object to eliminate the foregoing problems in the prior arts and to provide an improved immunologically measuring method which excels in the reproducibility of a measured value and makes it possible to quantitatively measure an immunologically active material contained in a specimen with a high accuracy.

Another object of the present invention is to provide an improved immunologically measuring method which makes it possible to quantitatively measure an immunologically active material such as antigen, antibody, etc. contained in a specimen with an improved accuracy by utilizing antigen-antibody reaction wherein a specific dehydrated immune reagent is used.

A further object of the present invention is to provide an improved immunologically measuring method which makes it possible to quantitatively measure an immunologically active material such as antigen, antibody, etc. contained in a specimen with an improved accuracy wherein a specific dehydrated immune reagent is used and the stirring upon preparing a dispersion of fine particles of said reagent by subjecting said fine particles to redispersion in a dispersing medium is properly controlled by optically observing the dispersed state of said fine particles, whereby causing agglutination reaction in a desirable state, and providing marked improvements in reproducibility and reliability of data obtained.

A further object of the present invention is to provide an improved immunologically measuring method which makes it possible to quantitatively measure an immunologically active material such as antigen, antibody, etc. contained in a specimen with an improved accuracy within a short period of time.

A still further object of the present invention is to provide an apparatus suitable for practicing the foregoing immunologically measuring method.

DETAILED DESCRIPTION OF THE INVENTION

Figure 1:
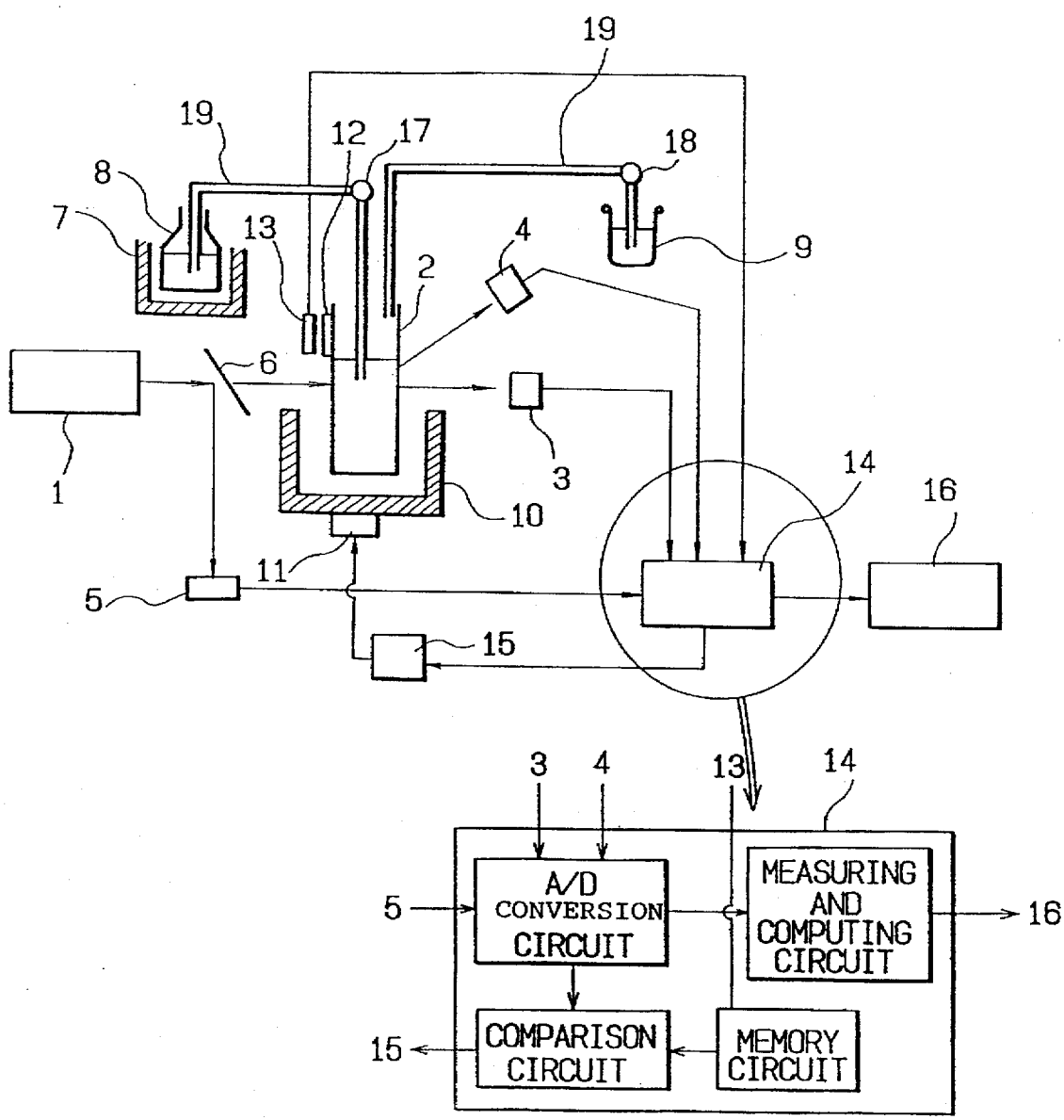
FIG. 1 is a schematic view of a typical example of the apparatus suitable for practicing the first embodiment of the immunologically measuring method according to the present invention.

The present inventors have intensively investigated the problems concerning the conventional measuring methods with dried reagents. Consequently it has been elucidated that the deviation of measured values by the conventional methods is caused by the change in the redispersed state, along with the decreased measuring sensitivity because the binding between solid fine particles and immunologically active materials is apparently damaged by long-term stirring for redispersion and too strong agitating power. The present inventors have furthermore carried out the investigations on the basis of the above results. It has been demonstrated that an extremely great effect would be brought about on highly sensitive and stable measurement, by stirring a dispersion medium while optically measuring the dispersion state during the step of redispersion of dried reagents, followed by transfer to next process at the time when an appropriate dispersion is achieved.

The present invention has been achieved as a result of further investigations based on the findings described above.

The present invention includes a method for measuring an immunological by active material (hereinafter referred to as immunologically measuring method"), which covers the two embodiments described below, and two apparatuses suitable for practicing each of the two embodiment.

The first embodiment of the immunologically measuring method according to the present invention relates to a method of optically measuring a degree of agglutination of a reaction mixture, produced by chemically or physically binding onto the surfaces of dehydrated solid particles a material immunologically active to a material to be measured in a sample, and reacting in a liquid medium the sample with the bound immunologically active material, which comprises the steps of:

(i) introducing a dispersion medium and the sample into a measuring cell containing the dehydrated solid fine particles (dried reagent fine particles) wherein the material immunologically active to the material to be measured in the sample is chemically or physically immobilized to the surfaces of the solid fine particles and dried:

(ii) optically measuring a dispersion state of the dried reagent particles in the dispersion medium, after stirring the dispersion medium, the dried reagent fine particles and the sample in the measuring cell;

(iii) terminating the stirring in the step (ii), at the time when the dispersion state of the dried reagent fine particles in the dispersion medium reaches a predetermined dispersion state, judging from the optically measured data obtained in the step (ii);

(iv) reacting together the dispersion containing the sample to produce an agglutination state, after the dispersion reaches the predetermined dispersion state in the step (iii);

(v) optically measuring the agglutination state of the reaction mixture produced in the step (iv).

The second embodiment of the immunologically measuring method according to the present invention relates to a method of optically measuring a degree of agglutination of a reaction mixture, produced by chemically or physically binding a material immunologically active to a material to be measured in a sample onto the surfaces of dried solid fine particles, and reacting in a liquid medium the sample with the bound immunologically active material, which comprises the steps of:

(i) introducing a dispersion medium and the sample to a reaction cell containing the dried solid particles (dried reagent fine particles) wherein the material immunologically active to the material to be measured in the sample is chemically or physically immobilized onto the surfaces of the solid fine particles and dried:

(ii) optically measuring dispersion state in the dispersion medium of the dried reagent fine particles, after stirring the dispersion medium, the dried reagent fine particles and the sample in the reaction cell;

(iii) terminating the stirring in the step (ii), at the time when the dispersion state of the dried reagent fine particles in the dispersion medium reaches a predetermined dispersion state, judging from the optically measured data obtained in the step (ii);

(iv) reacting together the dispersion containing the sample to produce an agglutination state, after the dispersion reaches the predetermined dispersion state in the step (iii);

(v) flowing the reaction mixture produced in the step (iv) into a measuring cell from the reaction cell;

(vi) optically measuring the degree of agglutination of the reaction mixture flown into the measuring cell.

A typical example of the apparatus suitable for practicing the first embodiment of the immunologically measuring method according to the present invention is an apparatus for optically measuring a degree of agglutination of a reaction mixture, produced by chemically or physically immobilizing a material immunologically active to a material to be measured in a sample onto the surfaces of dried solid fine particles, and reacting in a liquid medium the sample with immobilized immunologically active material, comprising a means to fix the measuring cell; a means to introduce the dispersion medium into the measuring cell; a means to introduce the sample into the measuring cell; a means to stir the contents in the measuring cell; a means to optically measure the degree of agglutination of the contents in the measuring cell; a means to determine a dispersion state of the dried reagent fine particles in the dispersion medium, based on the optically measured data of the mixture of dried reagent fine particles, the dispersion medium and the sample, and to control continuation and termination of the stirring.

A typical example of an apparatus suitable for practicing the second embodiment of the immunologically measuring method according to the present invention is an apparatus for optically measuring a degree of agglutination of a reaction mixture, produced by chemically or physically immobilizing a material immunologically active to a material to be measured in a sample onto the surfaces of dried solid fine particles, and reacting in a liquid medium the sample with the immobilized immunologically active material, said apparatus comprises a means to fix the reaction cell; a means to introduce a dispersion medium into the reaction cell; a means to introduce the sample in the reaction cell; a means to stir the contents in the reaction cell; a means to control continuation or termination of the stirring, based on the optically measured data obtained from the degree of agglutination of the dried reagent fine particles in the dispersion medium in the reaction cell; a means to fix a measuring cell to measure the degree of agglutination of the reaction mixture; a means to flow the reaction mixture into the measuring cell; a means to optically measure the degree of agglutination flown into the measuring cell.

According to the present invention, immunologically active materials in a sample, such as antigen and antibody, may be accurately determined, by using antigen-antibody reaction.

According to the present invention, the dried immunoreagent is used, so that the following merits may be obtained concerning reagent storage, compared with the storage of conventional reagents dispersed in water. That is, spontaneous agglutination over time as is observed in the case of reagents dispersed in water may not occur because the present reagent is in dry state; temperature control in storage of such reagent may be relaxed, (on the other hand, the conventional reagents cannot be frozen, special care should be taken of their storage.); the present dried reagent may be stored for a long term owing to its stability.

Furthermore, according to the present invention, the dry immunoreagent with the advantages described above is used and a state of a dispersion medium containing the fine particles of the reagent and a sample is optically measured during a stirring process of the dispersion medium; furthermore by controlling the stirring competence, the subsequent agglutination is smoothly facilitated, whereby the reproducibility and reliability of the data to be obtained may be greatly enhanced.

Still furthermore, according to the present invention, the process for stirring the reagent may be controlled to a minimum agitation time, so that the decrease in the sensitivity may be avoided and the measuring time may be shortened as well.

The present invention will now be explained specifically.

The solid fine particles to be used in the invention include particles from organisms, inorganic particles and organic particles. The particles from organisms include, for example, bacteria through dispersion treatment into erythrocytes, including Staphylococcus sp., Streptococcus sp., etc.. The inorganic particles include, for example, silica, alumina, bentonite, etc.. The organic particles include, for example, particles of homopolymer and/or copolymer of vinyl monomers such as styrene, vinylchloride, acrylonitrile, vinylacetate, acrylic acid ester, methacrylate ester, etc.; and particles of butadiene copolymer such as styrene-butadiene copolymer, methyl-methacrylate-butadiene copolymer, etc.. The size of any particle of particles from organisms, inorganic particles, and organic particles, may preferably be in the range of 0.05 to 5 μm and more preferably in the range of 0.1 to 2 μm. The dry reagent of a particle size less than 0.05 μm is hard to be dispersed, while the stability of a dispersed reagent of a particle size of more than 10 μm will be reduced.

The immunologically active material immobilized onto the surfaces of the solid particles include immunoglobulins such as IgG, IgM, IgE, etc.; plasma proteins such as complements, CRP, ferritin, $\alpha_1$-microglobulin and $\beta_2$-microglobulin and their respective antibodies; tumor markers such as $\alpha$-fetoprotein, carcinoembryonic antigen (CEA), prostatic acid phosphatase (PAP), CA19-9, CA-125, etc. and their respective antibodies; hormones such as luteinizing hormone (LH), follicle stimulating hormone (FSH), human chorionic gonadotropin (hCG), estrogen, insulin, etc.; and their respective antibodies; substances associated with virus infection such as HBV related antigens (HBs, HBe and HBc), HIV, ATL, etc. and their respective antibodies; bacteria such as *Corynebacterium diphtheriae, Clostridium botulinum*, mycoplasma, *Treponema pallidum*, etc. and their respective antibodies; protozoa such as *Toxoplasma gondii, Trichomonas leichmainiae*, Trypanosoma, Plasmodium, etc. and their respective antibodies; drugs including antiepileptics such as phenytoin and phenobarbital, cardiovascular agents such as quinidine and digoxin, antiasthmatics such as theophylline, antibiotics such as chloramphenicol, gentamycin, etc. and their respective antibodies; enzymes and exotoxin (for example, streptolysine O), and their respective antibodies. A substance which can induce antigen-antibody reaction with a material to be measured in a sample should be appropriately selected among them, depending on the sample type for use.

Among these immunologically active materials, hCG antibody, CRP antibody $\beta_2$-microglobulin antibody or $\alpha$-fetoprotein may specifically be preferable.

The technique for immobilizing immunologically active materials onto the surfaces of the solid fine particles may utilize physical adsorption or chemical bonding, but chemical bonding may be preferable in the present invention. That is, according to the present invention, the dry solid fine particles whose surfaces being immobilized with immunologically active materials are dispersed together with a sample as an agglutination factor, by strong stirring. Therefore, the immunologically active materials may occasionally be released from the solid particles, if they are immobilized by the immobilization technique utilizing physical adsorption with weak bonding strength. The immobilization technique by chemical bonding is carried out by the known method comprising chemically binding the protein which is contained as a component in an immunologically active material, to an antibody (see Immobilization Enzymes, ed. Ichiro Chihata, Kodansha (1975)). By using carbodiimide as a condensation agent, an immunologically active material may be immobilized to the solid particles where a functional group such as amino group and carboxyl group is present (see Japanese Patent Publication No. 12966/1978 or Japanese Unexamined Patent Publication No. 52620/1978).

By using polyaldehyde such as glutalaldehyde, an immunologically active material may be immobilized through covalent bonding to the latex particles containing carbamoyl group or amino group. By using cyanogen bromide, an immunologically active material may be immobilized through covalent bonding to the solid particles containing hydroxyl group. An immunologically active material may be reacted directly with the solid particles containing epoxy group or aldehyde group and immobilized through covalent bonding thereto.

Any bonding reaction described above for immobilizing an immunologically active material to solid fine particles may preferably be carried out in water or a mixed solvent of water with an organic solvent compatible with water, including alcohols, ketones, etc.. In order to stabilize the particles or to prevent the induction of nonspecific agglutination, there may preferably be added buffers such as phosphate buffer-physiological saline, Tris-HCF1 buffer, inactive proteins such as bovine serum albumin, etc., surfactants and the like, to the reaction system. The reaction solution preferably has pH of 6-10, more preferably pH of 7-9. The concentration of particles in the reaction solution may be 0.01-2.0 wt %, generally.

A dried immunoreagent may be obtained by removing a dispersion medium to be used as a dispersant of the particles to which is bound the immunologically active material.

For maintaining the activity of an immunologically active material, it is advantageous to carry out the removal of the dispersion medium at 60° C. or less, preferably at 30° C. or less. The specifically preferable embodiment for removal of the dispersion medium is exemplified by its removal by freeze-drying, so that the sensitivity of the immunoreagent may be maintained thereby constantly high. The introduction of the dried immunoreagent into a measuring cell may be carried out by a process comprising placing a given amount of the dispersion of particles to which are bound immunologically active materials, and subsequently drying the contents in the cell in the aforementioned manner in order to remove the dispersion medium, or by placing in a measuring cell, a given amount of the dried immunoreagent after removal of the dispersion medium.

As the measuring cell, there may be used those made of materials such as transparent glass or plastics (for example, polystyrene, polymethylmethacrylate, polyvinyl chloride, polycarbonate, polysulfone).

As the dispersion medium for dispersing a dried immunoreagent in the measuring cell, there may be used water or a mixed solvent comprising water and an organic solvent compatible with water such as alcohols, ketones, etc. To the dispersion medium may be added also pH buffering agents, proteins, surfactants, water-soluble polymer compounds, etc., optically.

Because antigen-antibody reaction is generally susceptible to the effects of pH of a solvent, pH buffering agents may be added in order to adjust the solution to optimum pH for the reaction; for example, phosphate buffer and Tris-HC1 buffer may be used. Proteins may be added for the purpose of preventing nonspecific reactions; for example, bovine serum albumin, gelatin, etc. may be used.

Surfactants and water-soluble polymer compounds are effective as an auxiliary dispersant of a dried immunoreagent, for example, nonionic surfactants such as Tween 20, anionic surfactants, polyvinylalcohol, polyacrylamide, polyacrylic acid, hydroxyethylcellulose, etc. may be used. However, there additives may be used in the range without inhibiting the antigen-antibody agglutination.

The dried immunoreagent may be optionally diluted with a dispersion medium, depending on the measuring subject. The concentration of the solid may vary, depending on the type and size of a measuring cell to be used; generally, the concentration should be adjusted preferably to the range of 0.01-5 wt %, more preferably to the range of 0.05-2 wt %.

In order to stir a sample, a dispersion medium and a dried immunoreagent, there may be selected appropriately a method comprising injecting a given amount of the dispersion medium in a measuring cell or a reaction cell containing the sample and the dried immunoreagent, and inserting a stirring device therein for stirring, or a method comprising shaking the measuring cell.

Among others, it is preferable to carry out the treatment with ultrasonic agitation which is the most effective for dispersing particles. The ultrasonic wave to be used for ultrasonic stirring may generally have a frequency of 15 kHz to 50 kHz, depending on the type and size of a measuring cell or a reaction cell.

In the dispersion process, the degree of dispersion of an immunoreagent in a dispersion medium may be optically measured by using an optically measuring means, and there may be appropriately employed, for example, the method for measuring the intensity of transmitted light, the method for measuring the intensity of scattered light, the method for measuring each intensity of transmitted light and scattered light in combination.

In determining the dispersion degree based on the intensity of transmitted light, for example, the intensity of light transmitting through a measuring cell or a reaction cell reduces as the dispersion is promoted, and it remains almost constant after a uniform state of dispersion is achieved.

The present inventors have invented a method for determining a preferable dispersion state, on the basis of the results of the experiments described below. The method for determining the state is practiced by confirming that the relation between A and Ao is in the range defined in the following formula;

$$A/Ao \leq 1.1,$$

[wherein Ao is an index defined in the formula $\log I'o/I'=Ao$ where I'o is a predetermined intensity of incident light in a dispersion medium when monochromatic light passes through a measuring cell or a reaction cell containing a complete dispersion of dried reagent fine particles; I' is an intensity of transmitted and/or scattered light; and on the other hand, A is an index defined in the formula $\log Io/I=A$ where Io is a predetermined intensity of incident light in a dispersion medium when the monochromatic light passes through a measuring cell or a reaction cell which contains a dispersion of the dried reagent fine particles and which is obtained in the aforementioned step (ii) (in the first embodiment) or in the step (ii) (in the second embodiment); I is an intensity of transmitted and/or scattered light.

The experiments carried out by the present inventors and the findings obtained through the experiments will now be explained hereinafter.

The experiments 1-(1) and 1-(2) are associated with the first embodiment of the immunologically measuring method according to the present invention; the experiments 2-(1) and 2-(2) are associated with the second embodiment of the immunologically measuring method according to the present invention.

Experiment 1-(1)

Figure 5:
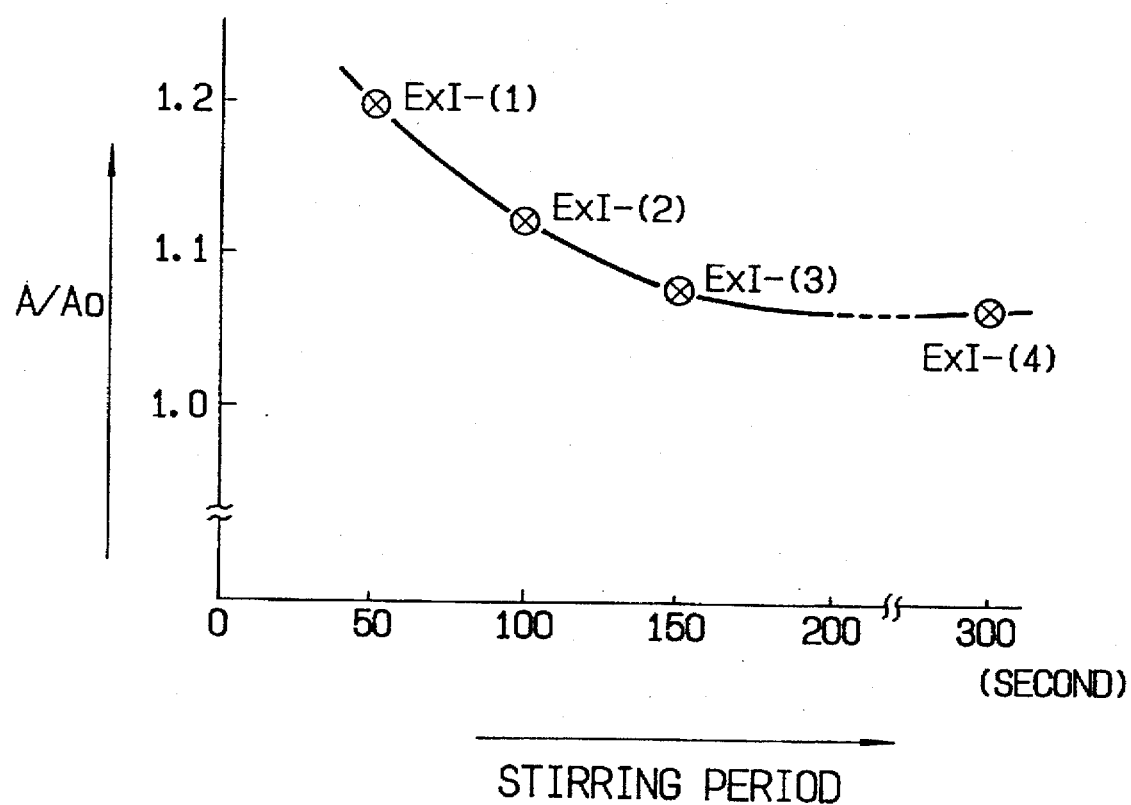
FIG. 5 and 6 represent the relation between stirring period and the ratio of A/Ao in Experiments 1-(1) and 1-(2) described hereinafter, respectively, in association with the first embodiment of the immunologically measuring method according to the present invention.

A part of the CRP sensitized latex prepared in the same manner as in Example 1-(1) was adjusted of its solid concentration at 0.2% wt with phosphate buffer-physiological saline (referred to as PBS), pH 7.2, to which had been added 1% wt bovine serum albumin and 5% wt sucrose, and the resulting solution was placed in a glass optical cell (light pass length; 2 mm). Then, the index Ao was determined according to the method described above to be 1.02 (wavelength for measurement; 633 nm). After adding PBS to the CRP-detecting dried reagent fine particles which were obtained also in the same method as in Example 1-(1), to adjust their solid concentration at 0.2% wt, CRP standard serum (2 mg/dl) was added. The resulting solution was subjected to ultrasonic agitation, to determine the index A according to the method described above. After termination of agitation, the CRP concentration was measured by the rate method described hereinafter. The results are shown in Table 1 and FIG. 5.

Experiment 1-(2)

Figure 6:
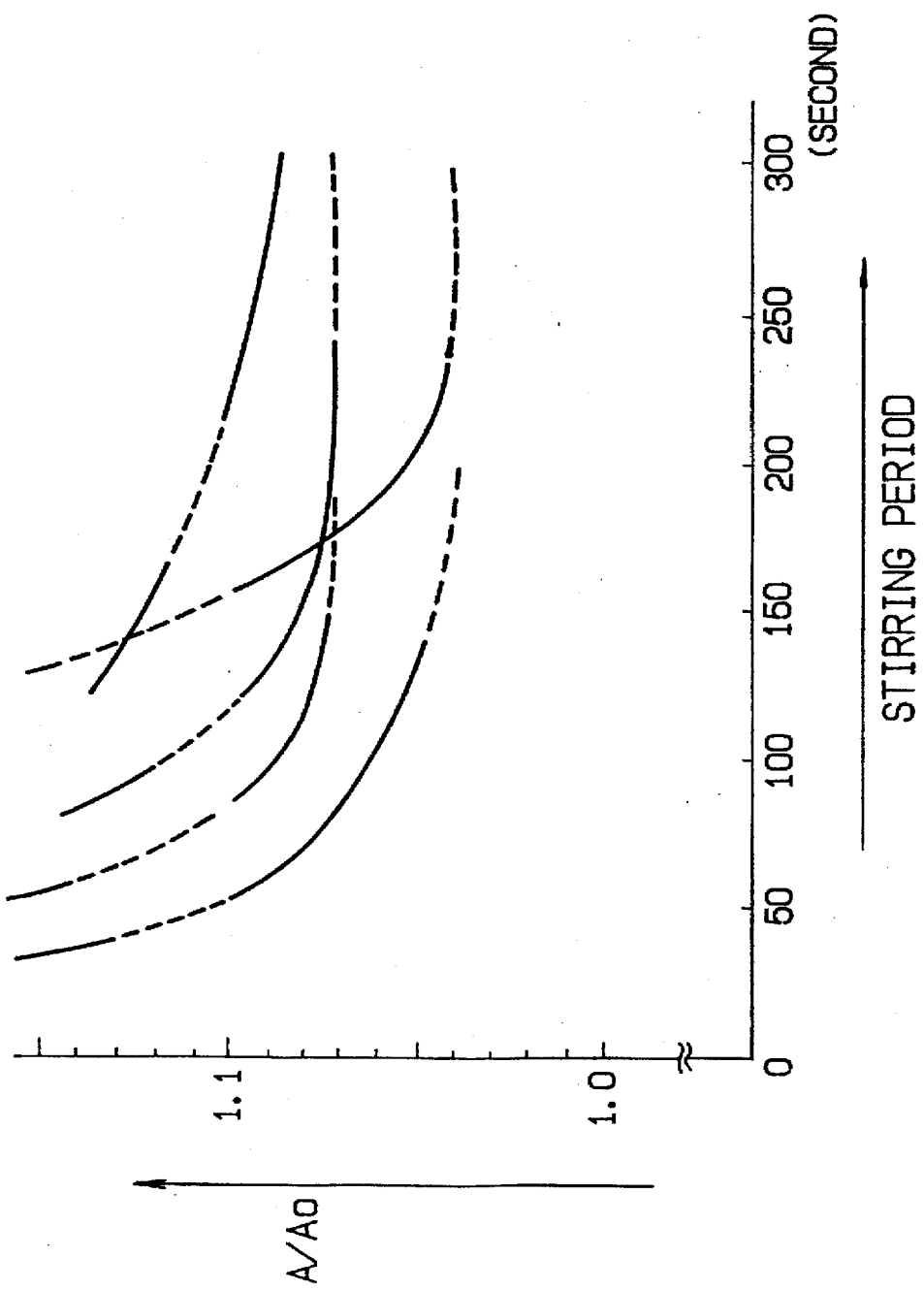

The same experiment was carried out as in Experiment 1-(1), except that solid fine particles with different compositions, of polystyrene, styrene-methacrylate copolymer, and polymethylmethacrylate, were used instead of carboxylated polystyrene and that the size of the fine particles was modified. The results are shown as plots in FIG. 6, where the stirring period is on the axis of abscissa and A/Ao is on the axis of ordinate. The part with poor measuring sensitivity is linked with solid line, while the part with slightly poor measuring sensitivity is linked with dotted line and the part with good sensitivity is linked with broad solid line.

Analysis based on the results obtained in Experiments 1-(1) and 1-(2)

As is clearly shown in Experiments 1-(1) and 1-(2), the measuring sensitivity is poor in the case of A/Ao more than 1.1. The experiments were repeated, and consequently, deviation of the measured values got larger when A/Ao exceeded 1.1. The value A/Ao=1.1 is found to be a critical value in terms of measuring sensitivity and deviation of measured values. The results shown in Table 1 indicate that the measuring sensitivity may tend to decline as the period of stirring treatment gets longer.

In other words, it is found that there can be established the stable measurement with a small deviation of any type of materials to be measured, even if they might be in a trace amount, by terminating the stirring during the stirring process of the dried reagent fine particles in a dispersion medium containing a sample when A/Ao achieves to satisfy the aforementioned range while performing optical measurement, followed by subsequent transfer into next process.

The first embodiment of the immunologically measuring method of the present invention has been achieved based on the findings described hereinabove.

In order to determine the index Ao concerning the complete dispersion of the dried reagent fine particles in the first embodiment, an immunologically active material is physically and/or chemically immobilized to solid fine particles in water or a mixed solvent principally composed of water, so that the dispersant composition of the sensitized reagent latex suspension, after immobilization and before drying process, may be made identical to a dispersant composition to be used in redispersion of the dried reagent fine particles and then the value of o Ao may be determined on the basis of the results of optical measurement.

During the stirring process including the dried reagent and a sample according to the present invention, the dispersion state was examined by the optical measurement described above while practicing the comparison between the obtained results of measurement of the dispersion state and the optical data demonstrating the predetermined dispersion state. Based on such results, the stirring process may be continued or terminated, or the stirring strength may be controlled.

When a sample contains a material reactive to the immunologically active material immobilized to the surfaces of the solid fine particles of a reagent, the immunologically active material reacts with the material to be measured, to induce antigen-antibody reaction and facilitate the agglutination, depending on the concentration of the material to be measured in the sample.

Alternatively, stirring may be done by inserting a stirring device in a measuring cell or by shaking a measuring cell, as long as the agglutinated masses do not dissociate.

It is preferable to carry out the stirring with a lower stirring competence, compared with that in the stirring process of the aforementioned dispersant containing the dried reagent and the sample.

The method for measuring the agglutination state by irradiating light to the reaction mixture in the measuring cell includes, for example, the method for measuring the intensity of transmitted light, the method for measuring the intensity of scattered light, the method in combination of these methods, and the method for measuring the density of integrating spheres.

The concentration of the material to be measured in the sample is calculated through data processing of the measured data by using, for example, known methods such as the rate assay method, and the end point technique (Immunological Procedure VIII, Bunko-do 2401 (1979)).

Figure 4:
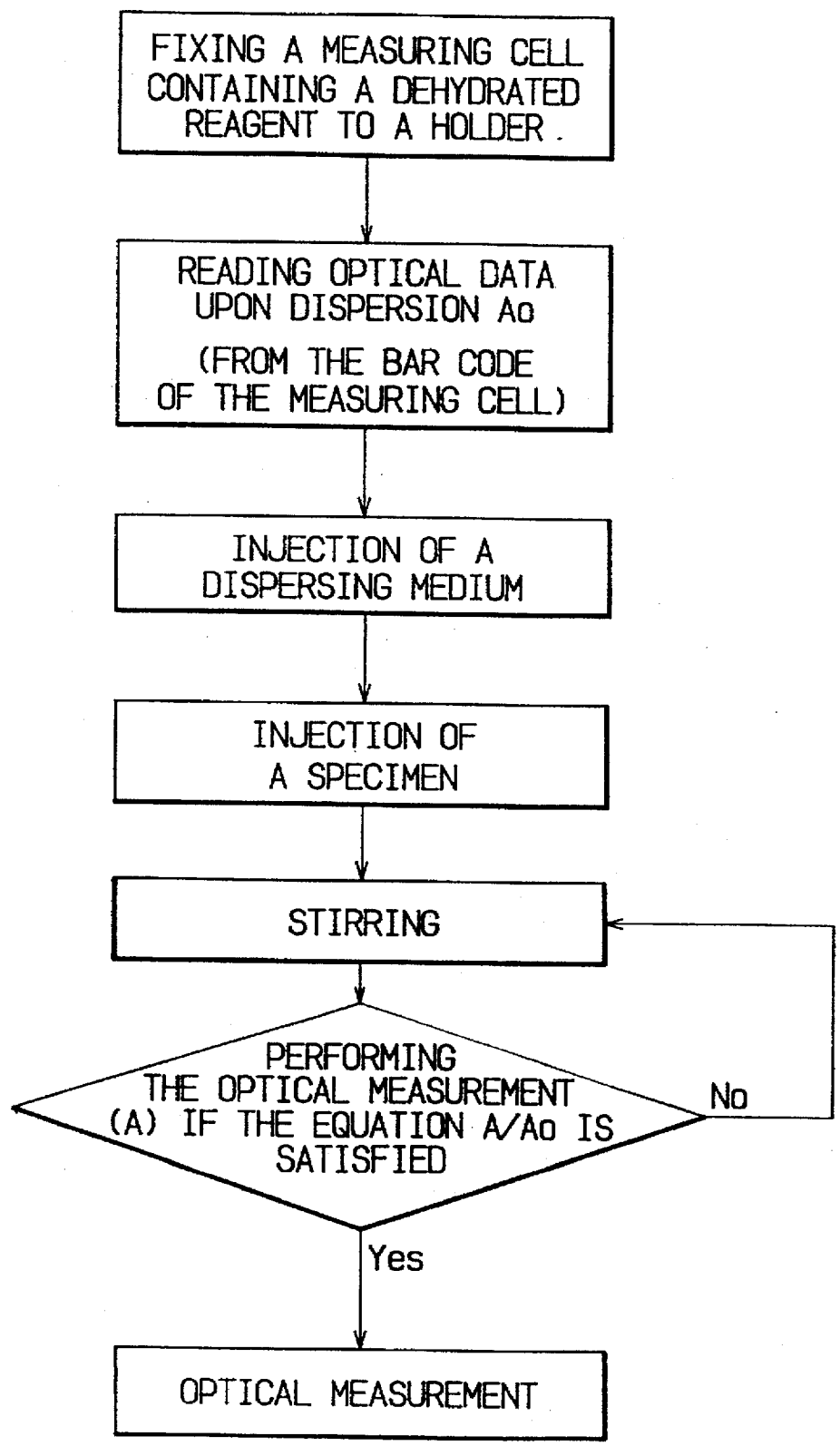
FIG. 4 is a flow chart representing the principle of the immunologically measuring method according to the present invention.

The principle of the measuring method of the present invention is shown in the flow chart in FIG. 4.

Experiment 2-(1)

Figure 7:
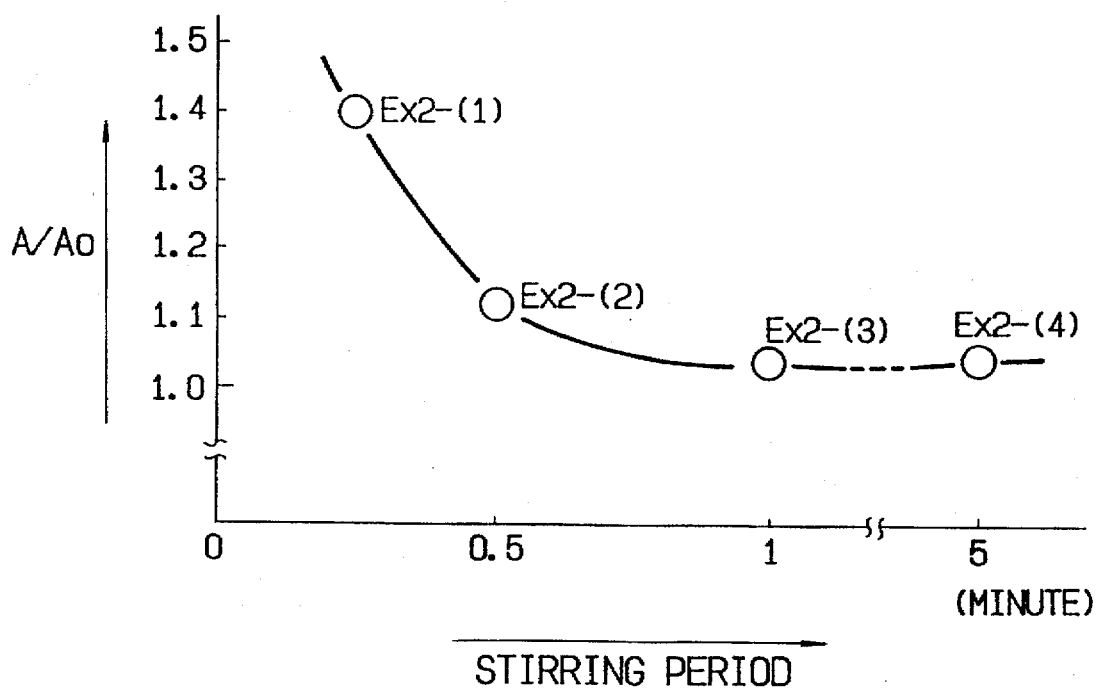
FIGS. 7 and 8 represent the relation between stirring period and the ratio of A/Ao in Experiments 2-(1) and 2-(2) described hereinafter, respectively, in association with the second embodiment of the immunologically measuring method according to the present invention.

A part of the CRP sensitized latex prepared in the same manner as in Example 2-(1) was adjusted of its solid concentration at 0.2% wt with phosphate buffer-physiological saline (referred to as PBS), pH 7.5, to which were added 1% wt bovine serum albumin and 5% wt sucrose, and the resulting solution was placed in a glass optical cell (light pass length; 2 mm). Then, the index Ao was determined according to the method described above to be 2.75 (wavelength for measurement; 633 nm). After adding PBS to the CRP-detecting dried reagent fine particles, which were obtained also in the same method as in Example 2-(1), to adjust their solid concentration at 0.2% wt, CRP standard serum (2 mg/dl) was added and the resulting solution was subjected to ultrasonic agitation, to determine the index A according to the method described above. Subsequently 60 seconds after termination of agitation, the reaction mixture was diluted, in a dilution cell, 500 fold with PBS and the resulting diluted solution was introduced into a flow cell. By irradiating Ar-laser to the flow cell to detect side-scattered light from the particles, the agglutination state of the reagent particles in the diluted solution was measured. The results were compared with a standard analytic curve preliminary prepared, to calculate the CRP concentration in the sample. The results are shown in Table 5 and FIG. 7. Experiment 2-(2)

Figure 8:
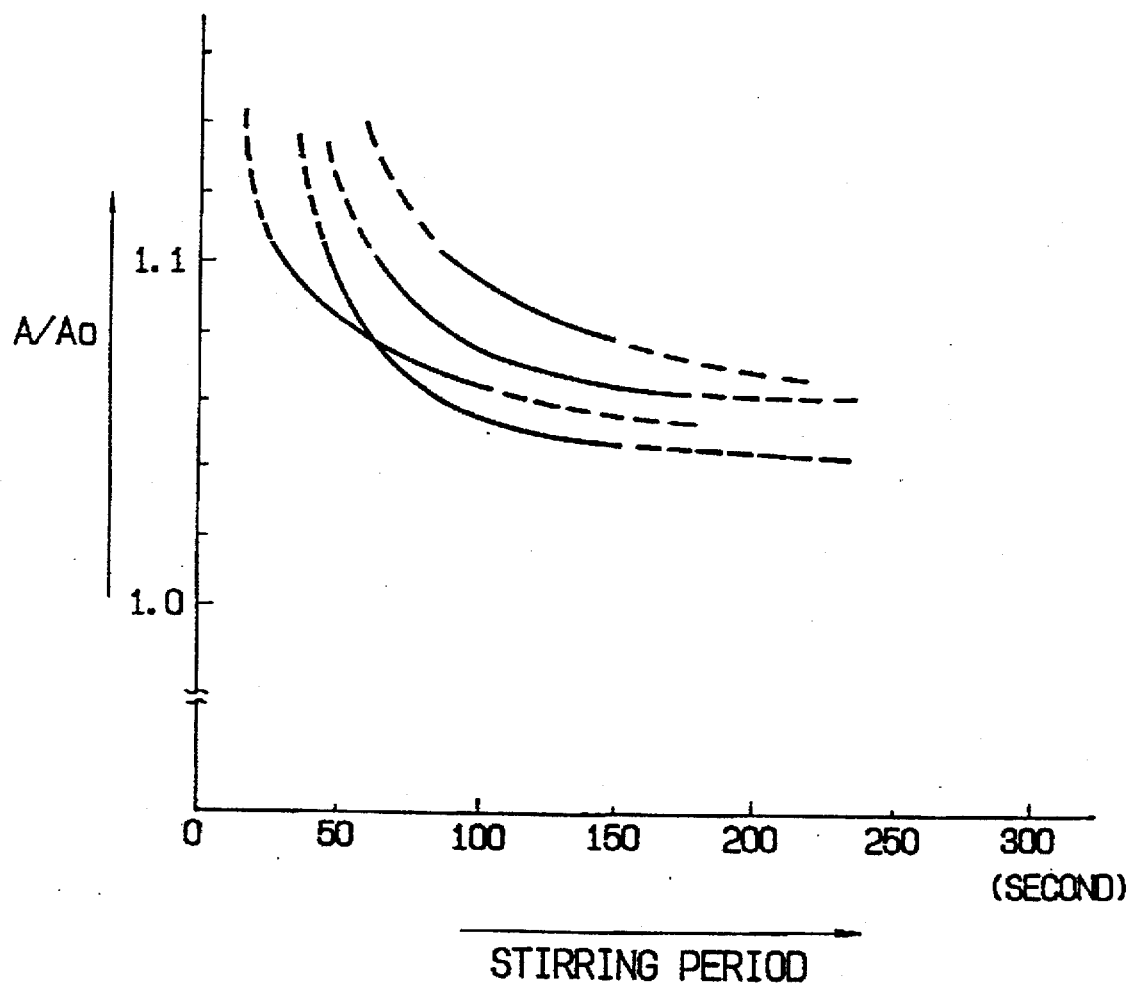

The same experiment was carried out as in Experiment 2-(1), except that solid fine particles with different compositions, of carboxylated styrene-methylmethacrylate copolymer, and plymethylmethacrylate, were used instead of carboxylated polystyrene and that the size of the solid fine particles was modified. The results are shown in FIG. 8, in which the part with good sensitivity and precision is linked with solid line, while other parts are linked with dotted line. Analysis based on the results obtained in Experiments 2-(1) and 2-(2)

As is clearly shown in Experiments 2-(1) and 2-(2), the measuring sensitivity is poor in the case of A/Ao more than 1.1. The same experiments were repeated and consequently, deviation of the measured values got larger when A/Ao exceeded 1.1. The value A/Ao=1.1 is found to be a critical value in terms of measuring sensitivity and deviation of measured values. The results shown in Table 5 indicate that the measuring sensitivity tends to decline as the agitation treatment is practiced for a longer time.

In other words, it is found that there can be established the stable measurement with a small deviation of any type of materials to be measured even if they might be in a trace amount, by terminating the stirring during the stirring process of the dried reagent fine particles in a dispersion medium containing a sample when A/Ao achieves to satisfy the aforementioned range while performing optical measurement, followed by subsequent transfer to next process.

The second embodiment of the immunologically measuring method of the present invention has been achieved based on the findings described hereinabove.

In order to determine the index Ao concerning the complete dispersion of the dried reagent fine particles in the second embodiment, an immunological active material is chemically or/and physically immobilized to solid fine particles in water or mixed solvent principally composed of water, so that the dispersant composition of the sensitized reagent latex suspension, after immobilization and before drying process, may be made identical to that of a dispersant to be used in redispersion of the dried reagent particles, and then the value of Ao may be determined on a basis of the results of optical measurement.

During the stirring process involving the dried reagent and a sample according to the present invention, the dispersion state is examined by the optical measurement described above while practicing the comparison between the results of measurement of the dispersion state obtained and the optical data demonstrating the predetermined dispersion states. Based on such results, the stirring process may be continued or terminated or the stirring competence may be controlled.

When a sample contains a material reactive to the immunologically active material bound to the surface of the particles in a reagent, the material to be measured reacts with the immunologically active material to induce antigen-antibody reaction to facilitate the agglutination, depending on the concentration of the material to be measured in the sample.

Alternatively, the stirring may be done by inserting a stirring device in a measuring cell or by shaking a measuring cell, as long as the agglutinated masses do not dissociate.

It is preferable to carry out the stirring with a weaker stirring strength, compared with that in the stirring process of the aforementioned dispersant containing the dried reagent and the sample.

The reaction mixture with agglutination facilitated in the reaction cell is diluted with the above dilution solution in a dilution cell. The concentration of the mixture should be adjusted to a concentration capable of transferring the agglutinated masses one by one in the subsequent process to introduce the resulting diluted reaction mixture into a flow cell.

The agglutination state of the diluted reaction mixture is determined by sequentially measuring optical reactions caused by agglutinated masses being introduced one by one into the flow cell. There may be preferably used, for example, flow cytometers of orthogonal optical axis-type and identical axis-type as disclosed in Diagnostic Test 30, (11) 1259.

The concentration of the material to be measured in the sample is calculated from the comparison of the agglutination state of the diluted reaction mixture comprising the sample and the reagent, with a standard analytic curve which is preliminary prepared and which represents the relation between the concentration of the material to be measured and the agglutination state of the diluted reaction mixture after completion of reaction.

The principle of the measuring method of the present invention is represented by the flow chart in FIG. 4.

The first embodiment and the second embodiment of the immunologically measuring method according to the present invention may be practiced by using an appropriate apparatus independently.

There will now be explained such apparatus.

The apparatus to be used for practicing the first embodiment of immunologically measuring method according to the present invention is to be explained hereinafter.

The apparatus to be used for practicing the first embodiment of the immunologically measuring method according to the present invention is required at least to have the following constitution. That is, the apparatus has at least a means to fix a measuring cell, a means to introduce a dispersion medium into the measuring cell, a means to introduce a sample into the measuring cell, a means to stir the contents of the measuring cell with a stirring competence adjustable and a means to optically measure a degree of agglutination in the measuring cell. Furthermore, a means to automatically dilute a sample and a means to detect the presence of excess antigen (prozone phenomenon) may be added.

In FIG. 1, there is shown a representative apparatus suitable for practicing the first embodiment of the immunologically measuring method according to the present invention.

In FIG. 1, numeral reference 2 stands for an optical cell made of acrylic resin or quartz glass which contains dehydrated latex reagent. Numeral reference 12 stands for a bar code of the optical data for dispersing said latex reagent into a dispersing medium which is disposed on the upper exterior of said optical cell 2. The optical cell 2 is placed in a constant temperature vessel 10 which is capable of serving as a holder therefor. The vessel 10 is equipped with a stirring means 11 including an ultrasonic vibrator capable of providing a vibration stirring function and a shaking means capable of providing a shaking stirring function. The optical data of the bar code 12 disposed on the exterior of the optical cell 2 is read by a bar code reading device 13. The optical data read out by the device 13 is transmitted to a data processing device 14, by which the data are memorized. Numeral reference 8 stands for a reservoir containing a dispersing medium. The reservoir 8 is placed in a constant temperature vessel 7. A predetermined amount of the dispersing medium contained in the vessel 7 is introduced through a transporting pipe 19 equipped with a liquid supplying pump 17 into the optical cell 2. The dehydrated latex reagent and the dispersing medium contained in the optical cell 2 placed in the constant temperature vessel 10 are stirred by actuating the ultrasonic vibrator. Numeral reference 1 stands for a light source for radiating light for optical measurement. Numeral reference 6 stands for a half mirror. Beam of light from the light source 1 is supplied into the optical cell 2. As the light source 1 in the case of radiating coherent light, there is used either He—Ne gas laser (wavelength: 632.8 nm) or semiconductor laser (wavelength: 780 nm or 830 nm). Other than these, it is possible use a tungsten lamp or a halogen lamp. In this case, an appropriate wavelength is selected by a monochrometer or a filter. The beam of light supplied into the optical cell 2 is dispersed or absorbed, and light transmitted through the cell is detected by a photomultiplier 3 and light scattered through the cell is detected by a photomultiplier 4. Variation in the light quantity for the light source is detected by a photomultiplier 5, and the signal detected by the photomultiplier 5 is transmitted to the data processing device 14. Likewise, the signal detected by the photomultiplier 3 and the signal detected by the photomultiplier 4 are transmitted to the data processing device 14.

These signals transmitted to the data processing device 14 are entered through a A/D conversion circuit into a comparison circuit wherein they are compared with the optical data concerning the dispersion of the latex reagent from a memory circuit. The compared signal is transmitted to a control device 15 for the ultrasonic vibrator in the stirring means 11 to demand termination or continuation of the ultrasonic vibration stirring or to control the competence of the ultrasonic vibration stirring. Upon terminating the stirring step, a specimen containing a material to be measured which is contained in a container 9 is introduced through a transporting pipe 19 equipped with a liquid supplying pump 18 into the optical cell 2. The contents in the optical cell 2 is shake-stirred by actuating the shaking means in the stirring means 11 for a predetermined period of time (for example, for 3 to 5 seconds) and subjected to the optical measurement in the same manner as in the above case.

After a predetermined period of time (for example, after a period of 20 seconds to 2 minutes), the same optical measurement is again performed. The signals resulted by the twice optical measurements are transmitted to the data processing device in the same way as in the above case, wherein they are entered through the A/D conversion circuit into a measuring and computing circuit wherein they are computatively processed based on the analytic curve data previously inputted thereinto, to thereby obtain concentration data which are digitally indicated on a display 16.

The apparatus to be used for practicing the second embodiment of the immunologically measuring method according to the present invention is to be explained hereinafter.

The apparatus to be used for practicing the second embodiment of the immunologically measuring method according to the present invention is required at least to have the following constitution. That is, the apparatus has at least a means to fix a reaction cell, a means to introduce a dispersion medium into the reaction cell, a means to introduce a sample into the reaction cell, a means to stir the contents of the reaction cell, a means to control continuation and termination of stirring, based on the optically measured data obtained from a dispersion state of the dried reagent particles in a dispersion medium, a means to fix a measuring cell to measure the degree of agglutination of a reaction mixture, a means to introduce the reaction mixture into the measuring cell, and a means to optically measure the degree of agglutination of individual aggregating particles of the reaction mixture poured into the measuring cell. Furthermore, the apparatus may be provided with a means to dilute the reaction mixture with a dilution solution before introducing the reaction mixture into the measuring cell. A means to detect a sample and a means to detect the presence of excess antigen (prozone phenomenon) may be added to such apparatus.

Figure 2:
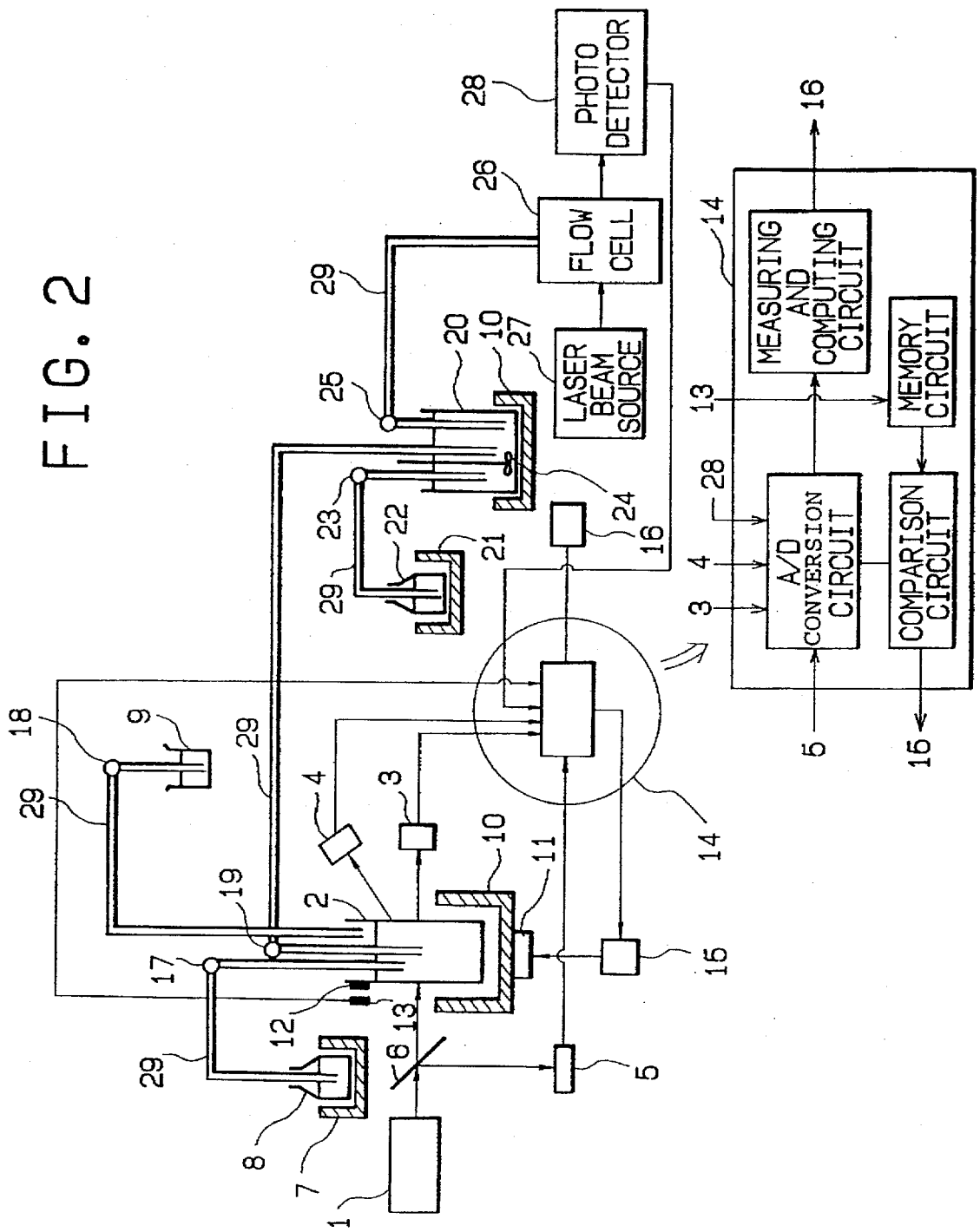
FIG. 2 is a schematic view of a typical example of the apparatus suitable for practicing the second embodiment of the immunologically measuring method according to the present invention.
Figure 3:
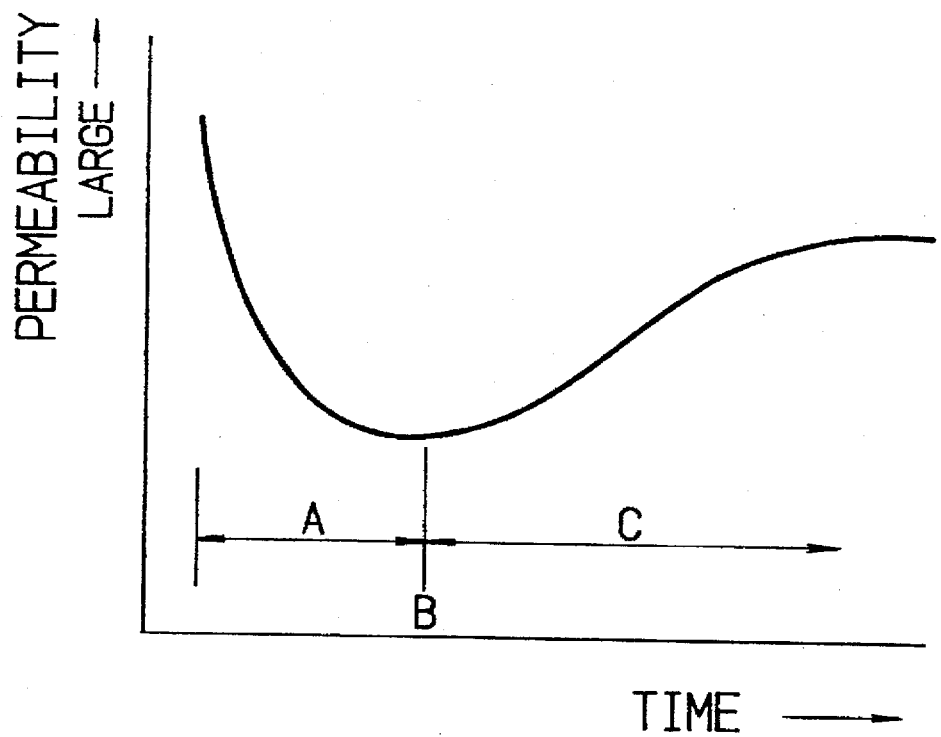
FIG. 3 represents transmission changes in respective steps of the immunologically measuring method according to the present invention.

A specific example of a preferable apparatus is shown in FIG. 2.

In FIG. 2, numeral reference 2 stands for an optical cell (reaction cell) made of acrylic resin or quartz glass which contains dehydrated latex reagent. Numeral reference 12 stands for a bar code which is disposed on the upper exterior of the reaction cell 2. The bar code 12 contains a code concerning the optical data for dispersing said latex reagent into a dispersing medium and a code for calling data of the reference standard analytic curve from a memory circuit. The reaction cell 2 is placed in a constant temperature vessel 10 which is capable of serving as a holder therefor. The vessel 10 is equipped with a stirring means 11 including an ultrasonic vibrator capable of providing a vibration stirring function and a shaking means capable of providing a shake-stirring function. The data of the bar code 12 disposed on the exterior of the optical cell 2 is read by a bar code reading device 13. The data read out by the device 13 is transmitted to a data processing device 14, by which the data are memorized. Numeral reference 8 stands for a reservoir containing a dispersing medium. The reservoir 8 is placed in a constant temperature vessel 7. A predetermined amount of the dispersing medium contained in the vessel 7 is introduced through a transporting pipe 29 equipped with a liquid supplying pump 17 into the reaction cell 2. The dehydrated latex reagent and the dispersing medium contained in the reaction cell 2 placed in the constant temperature vessel 10 are stirred by actuating the ultrasonic vibrator. Numeral reference 1 stands for a light source for radiating light for optical measurement. Numeral reference 6 stands for a half mirror. Beam of light from the light source 1 is supplied into the reaction cell 2. As the light source 1 in the case of radiating coherent light, there is used either He—Ne gas laser (wavelength: 632.8 nm) or semiconductor laser (wavelength: 780 nm or 830 nm). Other than these, it is possible use a tungsten lamp or a halogen lamp. In this case, an appropriate wavelength is selected by a monochrometer or a filter. The beam of light supplied into the reaction cell 2 is dispersed or absorbed, and light transmitted through the cell is detected by a photomultiplier 3 and light scattered through the cell is detected by a photomultiplier 4. Variation in the light quantity for the light source 1 is detected by a photomultiplier 5, and the signal detected by the photomultiplier 5 is transmitted to the data processing device 14. Likewise, the signal detected by the photomultiplier 3 and the signal detected by the photomultiplier 4 are transmitted to the data processing device 14.

These signals transmitted to the data processing device 14 are entered through a A/D conversion circuit into a comparison circuit wherein they are compared with the optical data concerning the dispersion of the latex reagent from a memory circuit. The compared signal is transmitted to a control device 15 for the ultrasonic vibrator in the stirring means 11 to demand termination or continuation of the ultrasonic vibration stirring or to control the competence of the ultrasonic vibration stirring. Upon terminating the stirring step, a specimen containing a material to be measured which is contained in a container 9 is introduced through a transporting pipe 29 equipped with a liquid supplying pump 18 into the reaction cell 2. The contents in the reaction cell 2 is shake-stirred by actuating the shaking means in the stirring means 11 for a predetermined period of time (for example, for 3 to 5 seconds) to cause agglutination reaction. The reaction mixture caused in the reaction cell is sent to a dilution cell 20 placed in a constant temperature vessel 10 through a transporting pipe 29 equipped with a liquid supplying pump 19, in accordance with the conditions under which the foregoing reference standard analytic curve. At the same time, a predetermined amount of a diluent contained in a reservoir 22 placed in a constant temperature vessel 21 is supplied into the dilution cell 20 through a transporting pipe 29 equipped with a liquid supplying pump 23. The reaction mixture and the diluent thus introduced into the dilution cell 20 are uniformly mixed by stirring them by a stirring means 24. Thus, the reaction mixture is diluted to a predetermined dilution degree. The admixture of the reaction mixture with the diluent in the dilution cell 20 may be performed by stirring them using the foregoing ultrasonic vibration stirring means or shake-stirring means. In this case, such stirring means is provided to the constant temperature vessel 10 (not shown).

The reaction mixture thus diluted in the dilution cell is sent a flow cell 26 through a transporting pipe 29 equipped with liquid supplying pump 25. In this case, the diluted reaction mixture is flown such that each of the aggregates of the reaction mixture individually passes through the flow cell 26 and side-scattered light caused by radiating laser beam from a laser beam source when each of the aggregates passes through the flow cell 26 can be detected by a photomultiplier 28. The signals detected by the photomultiplier are transmitted to the data processing device 14, wherein they are entered through the A/D conversion circuit into a measuring and computing circuit wherein they are computatively processed based on the analytic curve data previously inputted thereinto, to thereby obtain concentration data which are digitally indicated on a display 16.

DESCRIPTION OF THE PREFERRED EMBODIMENTS

The invention will be described more specifically while referring to the following Examples, which are not intended to restrict the scope of the invention only to these Examples.

Examples 1-(1) to 1-(4) described hereinafter are associated with the first embodiment of the present invention; Examples 2-(1) to 2-(4) described hereinafter are associated with the second embodiment of the present invention.

EXAMPLE 1-(1)

In this example, there was used the apparatus shown in FIG. 1.

Preparation of antibody sensitized suspension:

Goat anti-human CRP serum (manufactured by Bio Makor) was purified by chromatography on a column loaded with Protein-A Sepharose (manufactured by Pharmacia) into IgG fraction, which was then diluted to a concentration of 10 mg/ml with 0.1M phosphate buffer, pH 5.5.

To 10 ml of an aqueous suspension of 10% carboxylated polystyrene of 0.37 nm in particle size (manufactured by Nippon Synthetic Rubber K.K.) were sequentially added 25 ml of an aqueous 1% 1-cyclohexyl-3-[2-morpholyl-(4)-ethyl]carbodiimide metho-p-toluenesulfonate (referred to as carbodiimide Ts, hereinafter) solution as a condensation agent and 20 ml of the antibody of the IgG fraction, and the resulting solution was then stirred at room temperature for three hours to obtain sensitized latex.

To the sensitized latex after centrifuge and washing was added phosphate buffer-physiological saline (referred to as PBS hereinafter), pH 7.2, which had been adjusted to contain 1% wt of bovine serum albumin and 3% wt of sucrose, to prepare a CRP antibody sensitized latex suspension.

Dehydration of the reagent:

The CRP antibody sensitized latex suspension prepared above was freeze-dried under reduced pressure in liquid nitrogen, to obtain dried reagent fine particles for detecting CRP.

Measurement and evaluation of reproducibility:

Standard CRP Serum (manufactured by Kyowa Yuka K.K.) was diluted with Tris-HCl buffer to adjust its concentration to 0.5 mg/dl.

PBS was added to 1.2 mg of the dried reagent fine particles placed in a glass optical cell (light pass length; 2 mm) to a final concentration of 2% as the solid reagent.

Additionally, 10 µl of CRP standard serum (2 mg/dl) was added into the cell. The contents in the cell were immediately subjected to ultrasonic agitation. During the agitation process, there was determined the index A defined in the equation:

$$\log I_o/I = A$$

[wherein Io is an intensity of incident light and I is an intensity of transmitted light, provided that the wavelength for measurement is $\lambda = 633$ nm].

Separately, the foregoing CRP antibody sensitized latex suspension manner was adjusted to a concentration of 0.2%, and the transmitted light was measured by the same method described above to determine the value of $\log I'_o/I'$, which was 1.02 (=Ao).

The stirring process was terminated when the A determined in the above manner satisfied the formula $A/Ao \leq 1.1$ ($A \leq 1.1$) and the change in absorbance $\Delta A$ was measured, 20 seconds and 200 seconds after the termination, by irradiating the light of 633 nm in wavelength. In order to examine within-reproducibility, the measurement was repeated continuously ten times. In order to examine the deviation among production lots of a dried reagent, the reagent lots, A, B and C, prepared independently on different days, were used to carry out the measurement ten times each.

COMPARATIVE EXAMPLE 1-(1)

The same procedure as in Example 1-(1) was performed to examine within-reproducibility and reproducibility among lots, except that the time for dispersion by ultrasonic bibration stirring was made constant during the dispersion process.

Results

The results of the tests to examine within-reproducibility of CRP, carried out in Example 1-(1) and Comparative Example 1-(1), are shown in Table 2. The results of the tests to examine reproducibility within production lots of the reagent is shown in Table 3.

The results shown in Table 2 indicate that data deviation is smaller in Example 1-(1) where the stirring period of time for the latex reagent is made adjustable under control than in each case of fixed stirring period of time of 100, 200 or 300 seconds. As is clearly shown in Comparative Example 1, the change in absorbance, $\Delta A$, becomes smaller as the agitation period gets longer; in other words, the sensitivity is lowered.

The results in Table 3 indicate that the change in A among production lots of the dried reagent is greatly reduced in Example 1-(1) than in Comparative Example 1-(1).

EXAMPLE 1-(2)

Measurement of hCG

In this example, there was used the apparatus shown in FIG. 1.

Preparation of antibody sensitized suspension:

Anti-hCG antibody (manufactured by Bio Makor) was purified by chromatography on a column loaded with Protein-A Sepharose (manufactured by Pharmacia) into IgG fraction, which was then diluted to a concentration of 10 mg/ml with 0.1M phosphate buffer of pH 7.2.

To 4 ml of an aqueous suspension of 10% carboxylated polystyrene of 0.37 µm in particle size (trade name: G0303; manufactured by Nippon Synthetic Rubber K.K.) were sequentially added 20 ml of an aqueous 1% carbodiimide Ts solution and 20 ml of the antibody of the IgG fraction, and the resulting solution was then stirred at room temperature for two hours to obtain latex sensitized with immobilized antibody.

To the sensitized latex, after centrifuge and washing, were added bovine serum albumin, sucrose and sodium carboxymethylcellulose, to final concentrations of 1%, 3% and 2%, respectively. Then, PBS was also added to redisperse the latex to prepare a hCG antibody sensitized latex suspension.

Dehydration of the reagent:

The hCG antibody sensitized latex suspension prepared above was freeze-dried under reduced pressure in liquid nitrogen, to obtain dried reagent fine particles for detecting hCG.

Measurement and evaluation of reproducibility:

PBS was added to 1.2 mg of the dried reagent fine particles placed in a glass optical cell (light pass length; 2 mm) to a final concentration of 0.2% as the solid reagent.

Additionally, 100 µl of a hCG standard solution, which was obtained by adjusting Standard manufactured by Nippon Chemical Research to a concentration of 10 IU/ml, was added into the cell. The contents in the cell were immediately subjected to ultrasonic agitation, which was terminated at the time when the index A satisfied the formula; $A/Ao \leq 1.1$, [wherein the index Ao of 0.2% hCG sensitized latex suspension was preliminary measured to be 0.94 at a wave length 633 nm]; that is $A \leq 1.03$. The stirring period of time during the process was 110 seconds. The change in absorbance, $\Delta A$, 20 seconds and 200 seconds after the termination, was measured with the irradiation of light 633 nm in wavelength. In order to examine within-reproducibility, the measurement was repeated ten times in total.

As in Example 1-(1), the coefficient of variation (C.V.) was calculated in percentage (%).

The results obtained are shown in Table 4.

COMPARATIVE EXAMPLE 1-(2)

The same procedure as in Example 1-(2) was performed to calculate coefficients of variation in order to examine within-reproducibility (repetition of the measurement ten time), except that the period of time for ultrasonic vibration stirring was made constant at 100 seconds or 200 seconds.

The results obtained are shown in Table 4.

EXAMPLE 1-(3)

Measurement of AFP

In this example, there was used the apparatus shown in FIG. 1.

Preparation of antibody sensitized suspension:

Horse anti-human α-fetoprotein (AFP) serum (manufactured by Midori Juji K.K.) was purified by chromatography on a column loaded with Protein-A Sepharose (manufactured by Pharmacia) into IgG fraction, which was then diluted to a concentration of 10 mg/ml with 0.1M phosphate buffer of pH 7.2, to obtain the antibody of the IgG fraction.

To 5 ml of an aqueous suspension of 10% carboxylated polystyrene of 0.37 µm in particle size (trade name: G0303; manufactured by Nippon Synthetic Rubber K.K.) were sequentially added 20 ml of an aqueous 1% carbodiimide Ts solution and 20 ml of the antibody of the IgG fraction, and the resulting solution was then stirred at room temperature for two hours to obtain antibody sensitized latex.

To the sensitized latex after centrifuge and washing were added bovine serum albumin and sucrose to final concentrations of 1% and 3%, respectively. PBS of pH 7.2 was also added to prepare an AFP antibody sensitized latex suspension.

Dehydration of the reagent:

The AFP antibody sensitized latex suspension prepared above was freeze-dried under reduced pressure in liquid nitrogen, to obtain dried reagent fine particles for detecting AFP.

Measurement and evaluation of reproducibility:

PBS was added to 1.2 mg of the dried reagent fine particles placed in a glass optical cell (light pass length; 2 mm) so that the final concentration of the reagent as solid might be 0.2% by weight.

Additionally, 20 µl of the AFP standard solution (150 ug/ml) was added into the cell. (The AFP standard solution was obtained by diluting Standard AFP Serum manufactured by Kyowa Yuka K.K. to the predetermined concentration with Tris-HCl buffer.) The contents in the cell were immediately subjected to ultrasonic agitation, which was terminated at the time when the index A satisfied the formula; $A/Ao \leq 1.1$, [wherein the index Ao of 0.2% AFP sensitized latex suspension was preliminary measured to be 0.98 at a wavelength 633 nm]; that is, $A \leq 1.08$. The stirring period of time during the process was 160 seconds. The change in absorbance, $\Delta A$, 20 seconds and 200 seconds after the termination, was measured with the irradiation of light of 633 nm in wavelength. In order to examine within-reproducibility, the measurement was repeated ten times in total.

As in Example 1-(1), the coefficient of variation (C.V.) was calculated in percentage (%).

The result obtained are shown in Table 4.

COMPARATIVE EXAMPLE 1-(3)

The same procedure as in Example 1-(3) was performed to calculate coefficients of variation in order to examine within-reproducibility (repetition of the measurement ten times), except that the period of time for ultrasonic vibration stirring was made constant at 100 seconds or 200 seconds.

The results obtained are shown in Table 4.

EXAMPLE 1-(4)

Measurement of $\beta_2$-microglobulin

In this example, there was used the apparatus shown in FIG. 1.

Preparation of antibody sensitized suspension:

Rabbit anti-$\beta_2$-microglobulin (manufactured by Bio Makor) was purified by chromatography on a column loaded with Protein-A Sepharose (manufactured by Pharmacia) into IgG fraction, which was then diluted to a concentration of 10 mg/ml with 0.1M phosphate buffer of pH 7.2, to obtain the antibody of the IgG fraction.

To 4 ml of an aqueous suspension of 10% carboxylated polystyrene of 0.37 µm in particle size (trade name: G0303; manufactured by Nippon Synthetic Rubber K.K.) were sequentially added 20 ml of an aqueous 1% carbodiimide Ts solution and 20 ml of the antibody of the IgG fraction, and the resulting solution was then stirred at room temperature for three hours to obtain antibody sensitized latex.

To the sensitized latex after centrifuge and washing were added bovine serum albumin and sucrose to final concentrations of 1% and 3%, respectively. PBS of pH 7.2 was also added to prepare a $\beta_2$-microblobulin antibody sensitized latex suspension.

Dehydration of the reagent:

The $\beta_2$-microglobulin antibody sensitized latex suspension prepared above was freeze-dried under reduced pressure in liquid nitrogen, to obtain dried reagent fine particles for detecting $\beta_2$-miroglobulin.

Measurement and evaluation of reproducibility:

PBS was added to 1.2 mg of the dried reagent fine particles for detecting $\beta_2$-microglobulin, which had been placed in a glass optical cell (light pass length; 2 mm), so that the final concentration of the reagent as solid might be 0.2% by weight.

Additionally, 20 µl of the $\beta_2$-microglobulin standard solution (5 µg/ml) was added into the cell (The $\beta_2$-microglobulin standard solution was obtained by diluting Standard $\beta_2$-microglobulin Serum manufactured by Kyowa Yuka K.K. to the predetermined concentration with Tris-HC1 buffer.) The contents in the cell were immediately subjected to ultrasonic agitation, which was terminated at the time when the index A satisfied the formula; $A/Ao = \leq 1.1$, [wherein the absorption index Ao of 0.2% $\beta_2$-microglobulin sensitized latex suspension was preliminary measured to be 1.04 at a wavelength 633 mm]; that is, $A \leq 1.14$. The stirring period of time during the process was 190 seconds. The change in absorbance, $\Delta A$, 20 seconds and 200 seconds after the termination, was measured with the irradiation of light of 633 nm in wavelength. In order to examine within-reproducibility, the measurement was repeated ten times in total. As in Example 1-(1), the coefficient of variation (C.V.) was calculated in percentage (%).

The results obtained are shown in Table 4.

COMPARATIVE EXAMPLE 1-(4)

The same procedure as in Example 1-(4) was performed to calculate coefficients of variation in order to examine within-reproducibility (repetition of the measurement ten times), except that the time for ultrasonic vibration stirring was made constant at 100 seconds or 200 seconds.

The results obtained are shown in Table 4.

Evaluation

The results shown in Table 4 indicate that data deviation is smaller in the Examples where the stirring period of time for the latex reagent is made adjustable under control than in each Comparative Example where the stirring period of time is fixed; namely that within-reproducibility is improved in the Examples, even if the material to be measured is changed to hCG, $\beta_2$-microglobulin and AFP.

EXAMPLE 2-(1)

Measurement of CRP

In this example, there was used the apparatus shown in FIG. 2.

Preparation of antibody sensitized suspension:

Goat anti-human CRP serum (manufactured by Bio Makor) was purified by chromatography on a column loaded with Protein-A Sepharose (manufactured by Pharmacia) into IgG fraction, which was then diluted to a concentration of 10 mg/ml with 0.1M phosphate buffer of pH 5.5.

The 10 ml of an aqueous suspension of 10% carboxylated polystyrene of 0.71 nm in particle size (trade name: G0701; manufactured by Nippon Synthetic Rubber K.K.) was added 25 ml of an aqueous 1% 1-cyclohexyl-3-[2-morpholyl-(4)-ethyl]carbodiimide metho-p-toluenesulfonate (referred to as carbodiimide Ts, hereinafter) solution as a condensation agent and 20 ml of the antibody of the IgG fraction, and the resulting solution was then stirred at room temperature for three hours to obtain sensitized latex.

After centrifuging and washing the sensitized latex, phosphate buffer-physiological saline of pH 7.2 (referred to as PBS hereinafter), which had been adjusted to contain 1% by weight of bovine serum albumin and 3% by weight of sucrose, was added to prepare a CRP antibody sensitized latex suspension.

Dehydration of the reagent:

The CRP antibody sensitized latex suspension prepared above was freeze-dried under reduced pressure in liquid nitrogen, to obtain dried reagent fine particles for detecting CRP.

Measurement and evaluation of reproducibility:

Standard CRP Serum (manufactured by Kyowa Yuka K.K.) was diluted with Tris-HC1 buffer to adjust its concentration to 5 ug/ml.

PBS was added to 1.2 mg of the dried reagent particles in a glass optical cell (light pass length; 2 mm) so that the concentration of the reagent as solid might be 0.2% by weight.

Additionally, 0.3 ml of the CRP antibody (5 µg/ml) was added into the cell. The contents in the cell were immediately subjected to ultrasonic agitation, and during the agitation process, there was determined the index A defined in the equation:

$$\log Io/I = A$$

[wherein Io is an intensity of incident light and I is an intensity of transmitted light, provided that the wave length to be measured is $\lambda = 633$ nm].

Separately, the foregoing CRP antibody sensitized latex suspension was adjusted to a concentration of 0.2%, and the transmitted light was measured by the same method described above to determine the value of $\log Io/I$, which was 2.75 ($= Ao$).

The stirring process was terminated when the A satisfied the formula $A/Ao \leq 1.1$ ($A \leq 3.03$), and 300 seconds later, the reaction mixture was diluted 500 fold with PBS and mixed together in a dilution cell (20-ml cell made of polyethylene terephalate). The diluted reaction mixture was injected into a flow cell and then, laser beam of 488 nm in wavelength irradiated the cell to measure the agglutination state of the particles in the diluted reaction mixture. The data were compared with the premeasured data from a standard analytic curve, to determine the CRP concentration in a CRP sample. The procedure was repeated ten times to examine the reproducibility.

COMPARATIVE EXAMPLE 2-(1)

The same procedure as in Example 2-(1) was performed to examine reproducibility, except that the period of time for dispersion by ultrasonic vibration stirring was made constant during the dispersion process.

Results

The results obtained in Example 2-(1) and Comparative Example 2-(1) are shown in Table 6.

The results obtained indicate that the measured values of the CRP concentration obtained by examining a dispersion state of the dried reagent and terminating the stirring when the dispersion state reached the predetermined state, approximate the real value (5.0 µg/ml) with the smallest deviation. In the case where the period of time with respect to stirring treatment is fixed at 15 seconds, the dried reagent won't disperse sufficiently so that the reagent particles do not disperse singly; in other words, the particles are already present in agglutination state before reaction with CRP, which increase an apparent measured value.

The stirring period fixed at 30 sec is almost identical to the stirring period of time as in Example 2-(1), but the deviation of the measured values of the CRP concentration is larger because the dispersion state is changeable on occasion. In the case where the stirring period is fixed at 300 sec, the dried reagent may disperse sufficiently, but the sensitivity gets lowered due to possible decrease in the antibody activity so that the measured values of CRP are smaller than the real value.

EXAMPLE 2-(2)

Measurement of hCG

In this example, there was used the apparatus shown in FIG. 2.

Preparation of antibody sensitized suspension:

Rabbit anti-hCG antibody (manufactured by Bio Makor) was purified by chromatography on a column loaded with Protein-A Sepharose (manufactured by Pharmacia) into IgG fraction, which was then diluted to a concentration of 10 mg/ml with 0.1M phosphate buffer of pH 7.2.

To 4 ml of an aqueous suspension of 10% carboxylated polystyrene of 0.71 nm in particle size (trade name: G0701; manufactured by Nippon Synthetic Rubber K.K.) were sequentially added 20 ml of an aqueous 1% carbodiimide Ts solution and 20 ml of the antibody of the IgG fraction, and the resulting solution was then stirred at room temperature for two hours to obtain latex sensitized with the immobilized antibody.

To the sensitized latex, after centrifuge and washing, were added bovine serum albumin, sucrose and sodium carboxymethylcellulose, to final concentrations of 1%, 3% and 2%, respectively. Then, PBS was also added to redisperse the latex to prepare a hCG antibody sensitized latex suspension.

Dehydration of the reagent:

The hCG antibody sensitized latex suspension prepared above was freeze-dried under reduced pressure in liquid nitrogen, to obtain dried reagent fine particles for detecting hCG.

Measurement and evaluation of reproducibility:

PBS was added to 1.2 mg of the dried reagent fine particles placed in a glass optical cell (light pass length; 2 mm) to a final concentration of 0.2% as the solid reagent.

Additionally, 100 μl of the hCG standard solution, which was obtained by adjusting Standard manufactured by Nippon Chemical Research to a concentration of 10 IU/ml, was added into the cell. The contents in the cell were immediately subjected to ultrasonic agitation, which was terminated at the time when the index A satisfied the formula; $A/Ao \leq 1.1$, [wherein the absorption index Ao of 0.2% hCg sensitized latex suspension was preliminary measured to be 2.81 at a wavelength 633 nm]; that is, $A \leq 3.09$. The stirring period of time during the process was 40 seconds. 300 seconds after the termination, the reaction mixture was diluted 500 fold with PBS and mixed together in a dilution cell (20-ml cell made of polyethylene terephthalate). The diluted reaction mixture was introduced into a flow cell, and then laser beam of 488 nm in wavelength irradiated the cell to measure the agglutination state of the particles in the diluted reaction mixture. The data were compared with the premeasured data from a standard analytic curve, to determine the hCG concentration in a hCG sample. The procedure was repeated ten times to examine the reproducibility.

The results obtained are shown in Table 7.

COMPARATIVE EXAMPLE 2-(2)

In order to examine reproducibility, the same procedure as in Example 2-(2) was performed to calculate coefficients of variation, except that the period of time for dispersion by ultrasonic vibration stirring was made constant (45 sec, 300 sec) during the dispersion process.

The results obtained are shown in Table 7.

EXAMPLE 2-(3)

Measurement of AFP

In this example, there was used the apparatus shown in FIG. 2.

Preparation of antibody sensitized suspension:

Horse anti-human α-fetoprotein (AFP) serum (manufactured by Midori Juji K.K.) was purified by chromatography on a column loaded with Protein-A Sepharose (manufactured by Pharmacia) into IgG fraction, which was then diluted to a concentration of 10 mg/ml with 0.1M phosphate buffer of pH 7.2 to obtain the antibody of the IgG fraction.

To 5 ml of an aqueous suspension of 10% carboxylated polystyrene of a 0.71 nm particle size (G0701; manufactured by Nippon Synthetic Rubber K.K.) were sequentially added 20 ml of an aqueous 1% carbodiimide Ts solution and 20 ml of the antibody of the IgG fraction, and the resulting solution was then stirred at room temperature for two hours to obtain antibody sensitized latex.

To the sensitized latex, after centrifuge and washing, were added bovine serum albumin and sucrose to final concentrations of 1% and 3%, respectively. PBS, pH 7.2, was also added to prepare an AFP antibody sensitized latex suspension.

Dehydration of the reagent:

The AFP antibody sensitized latex suspension prepared above was freeze-dried under reduced pressure in liquid nitrogen, to obtain dried reagent fine particles for detecting AFP.

Measurement and evaluation of reproducibility:

PBS was added to 1.2 mg of the dried reagent fine particles for detecting AFP, which was placed in a glass optical cell (light pass length; 2 mm) so that the final concentration of the reagent as solid might be 0.2% by weight.

Additionally, 200 μl of the AFP standard solution (50 μg/ml) was added into the cell. (The AFP standard solution was obtained by diluting Standard AFP Serum manufactured by Kyowa Yuka K.K. to a predetermined concentration with Tris-HCl buffer.) The contents in the cell were immediately subjected to ultrasonic agitation, which was terminated at the time when the absorption index A satisfied the formula; $A/Ao \leq 1.1$, wherein the absorption index Ao of 0.2% AFP sensitized latex suspension was preliminary measured to be 2.71 at a wavelength 633 nm]; that is, $A \leq 2.98$. The stirring period of time during the process was 30 seconds.

Subsequently 300 seconds after the termination, the reaction mixture was diluted 500 fold with PBS and mixed together in a dilution cell (20-ml cell made of polyethylene terephthalate). The diluted reaction mixture was introduced into a flow cell, and then laser beam of 488 nm in wavelength irradiated the cell to measure the agglutination state of the particles in the diluted reaction mixture. The data were compared with the premeasured data from a standard analytic curve, to determine the AFP concentration in an AFP sample. The procedure was repeated ten times to examine the reproducibility.

The results obtained are shown in Table 7.

COMPARATIVE EXAMPLE 2-(3)

In order to examine reproducibility (repetition of the measurement ten times), the same procedure as in Example 2-(3) was performed to calculate coefficients of variation, except that the time for dispersion by ultrasonics was made constant at 30 sec or 300 sec during the dispersion process.

The results obtained are shown in Table 7.

EXAMPLE 2-(4)

Measurement of $\beta_2$-microglobulin

In this example, there was used the apparatus shown in FIG. 2.

Preparation of antibody sensitized suspension:

Rabbit anti-$\beta_2$-microglobulin (manufactured by Bio Makor) was purified by chromatography on a column loaded with Protein-A Sepharose (manufactured by Pharmacia) into IgG fraction, which was then diluted to a concentration of 10 mg/ml with 0.1M phosphate buffer of pH 7.2, to obtain the antibody of the IgG fraction.

To 4 ml of an aqueous suspension of 10% carboxylated polystyrene of 0.71 nm in particle size (trade name: G0701; manufactured by Nippon Synthetic Rubber K.K.) were sequentially added 20 ml of an aqueous 1% carbodiimide Ts solution and 20 ml of the antibody of the IgG fraction, and the resulting solution was then stirred at room temperature for three hours to obtain antibody sensitized latex.

To the sensitized latex, after centrifuge and washing, were added bovine serum albumin and sucrose to final concentrations of 1%, 3%, respectively. PBS of pH 5.5 was also added to prepare a $\beta_2$-microglobulin antibody sensitized latex suspension.

Dehydration of the reagent:

The $\beta_2$-microglobulin antibody sensitized latex suspension prepared above was freeze-dried under reduced pressure in liquid nitrogen, to obtain dried reagent fine particles for detecting $\beta_2$-microglobulin.

Measurement and evaluation:

PBS was added to 1.2 mg of the dried reagent fine particles for detecting $\beta_2$-microglobulin, in a glass optical cell (light pass length; 2 mm) so that to a final concentration of the reagent as solid might be 0.2% by weight.

Additionally, 100 µl of the $\beta_2$-microglobulin standard solution, of 5 µg/ml (referred to as MG sample) was added into the cell (The MG sample was obtained by diluting Standard $\beta_2$-microglobulin Serum manufactured by Kyowa Yuka K.K. to the predetermined concentration with Tris-HCl buffer.) The contents in the cell were immediately subjected to ultrasonic agitation, which was terminated at the time when the absorption index A satisfied the formula; $A/Ao \leq 1.1$, [wherein the absorption index Ao of 0.2% $\beta_2$-microglobulin sensitized latex suspension was preliminary measured to be 2.80 at a wavelength 633 nm]; that is, $A \leq 3.06$. The stirring period of time during the process was 40 seconds. Subsequently 300 seconds after the termination, the reaction mixture was diluted 500 fold with PBS and mixed together in a dilution cell (20-ml cell made of polyethylene terephthalate). The diluted reaction mixture was introduced into a flow cell, and then laser beam of 488 nm in wavelength irradiated the cell to measure the agglutination state of the particles in the diluted reaction mixture. The data were compared with the premeasured data from a standard curve, to determine the $\beta_2$-microglobulin concentration in a MG sample. The procedure was repeated ten times to examine the reproducibility.

As in Example 2-(1), the coefficient of variation, C.V., was calculated in percentage (%).

The results obtained are shown in Table 7.

COMPARATIVE EXAMPLE 2-(4)

The same procedure as in Example 4 was performed to calculate coefficients of variation in order to examine reproducibility (repetition of the measurement ten times), except that the stirring period of time for dispersion by ultrasonic vibration stirring was made constant at 35 sec or 300 sec during the dispersion process.

The results obtained are shown in Table 7.

Evaluation

The results shown in Table 7 indicate that there may be obtained the measured data more closely approximating the real value with a smaller deviation in the Examples where the agitation time of latex reagent is adjustable under control, than in each Comparative Example where the agitation time is fixed; namely that within-reproducibility is improved in the Examples, even if the material to be measured is changed to hCG, $\beta_2$-microglobulin and AFP.

TABLE 1

| Sample No. | A/Ao | Measuring Sensitivity |
|---|---|---|
| Ex I - | | |
| (1) | 1.25 | x |
| (2) | 1.12 | Δ |
| (3) | 1.08 | o |
| (4) | 1.07 | Δ | o: Good
Δ: Practically acceptable
x: Practically not acceptable

TABLE 2

| CONCURRENT REPROPUCIBUTY TEST (same reagent lot) | | | | |
|---|---|---|---|---|
| | Example 1-(1) | Comparative Example 1-(1) | | |
| Stirring period | varied (80 to 230 sec.) 130 sec. on average | 100 sec. (fixed) | 200 sec. (fixed) | 300 sec. (fixed) |
| Measured Cycle(times)(N) | 10 | 10 | 10 | 10 |
| Mean value$\Delta A$ ($\bar{x}$) | 0.191 | 0.198 | 0.184 | 0.179 |
| Standard deviation (S.D.) | $5.3 \times 10^{-3}$ | $1.5 \times 10^{-2}$ | $7.2 \times 10^{-3}$ | $5.4 \times 10^{-3}$ |
| Coefficient of variation (C.V. %)* | 2.8 | 7.6 | 3.9 | 3.0 |

*$C.V.(\%) = \frac{S.D.}{\bar{x}} \times 100$

TABLE 3

| CONCURENT REPROPUCIBUTY TEST BETWEEN REAGENT PRODUCTION LOTS | | | | | | |
|---|---|---|---|---|---|---|
| Reagent production | Example 1-(1) | | | Comparative Example 1-(1) | | |
| lot | A | B | C | A | B | C |
| Stirring period | varied (80 to 230 sec.) 130 sec. on average | varied (70 to 150 sec.) 105 sec. on average | varied (120 to 250 sec. 175 sec. on average | (fixed) 200 sec. | (fixed) 200 sec. | (fixed) 200 sec. |
| Mean | 0.191 | 0.183 | 0.179 | 0.184 | 0.162 | 0.166 |

TABLE 3-continued

CONCURENT REPROPUCIBUTY TEST BETWEEN REAGENT PRODUCTION LOTS

| Reagent production | Example 1-(1) | | | Comparative Example 1-(1) | | |
|---|---|---|---|---|---|---|
| lot | A | B | C | A | B | C |
| value$\Delta A$ ($\bar{x}$) | | | | | | |
| Standard deviation (S.D.) | $5.3 \times 10^{-3}$ | $5.7 \times 10^{-3}$ | $5.4 \times 10^{-3}$ | $7.2 \times 10^{-3}$ | $7.7 \times 10^{-3}$ | $9.8 \times 10^{-3}$ |
| Coefficient of variation (C.V.%) | 2.8 | 3.1 | 3.0 | 3.9 | 4.8 | 5.9 |

Nete Measured time: 10 times (N = 10)

TABLE 4

CONCURENT REPROPUCIBUTY TEST BETWEEN REAGENT PRODUCTION LOTS

| Material to be measured | | Stirring Period | Coefficient of Variation (C.V.%) |
|---|---|---|---|
| hCG | Example 1-(2) | varied (40 to 225 sec.) 120 sec. on average | 4.9 |
| | Comparative Example 1-(2) | (fixed) 100 sec. | 8.3 |
| | | (fixed) 200 sec. | 5.7 |
| AFP | Example 1-(3) | varied (80 to 240 sec.) 145 sec. on average | 5.4 |
| | Comparative Example 1-(3) | (fixed) 100 sec. | 9.7 |
| | | (fixed) 200 sec. | 6.0 |
| $\beta_2$-microglobulin | Example 1-(4) | varied (90 to 235 sec.) 155 sec. on average | 3.8 |
| | Comparative Example 1-(4) | (fixed) 100 sec. | 8.1 |
| | | (fixed) 200 sec. | 4.9 |

TABLE 5

| Sample No. | A/Ao | Measuring Sensitivity | Measuring Accuracy |
|---|---|---|---|
| Ex II - | | | |
| (1) | 1.40 | x | x |
| (2) | 1.12 | Δ | Δ |
| (3) | 1.06 | o | o |
| (4) | 1.04 | Δ | o | o: Good
Δ: Practically acceptable
x: Practically not acceptable

TABLE 6

| | Example 2-(1) | Comparative Example 2-(1) | | |
|---|---|---|---|---|
| Stirring Period | 26–37 sec. (32 sec. on average | 15 sec. | 30 sec. | 300 sec. |
| Measured Cycle(times) | 10 | 10 | 10 | 10 |
| A/Ao (average) | 1.09 | 1.59 | 1.24 | 1.05 |
| A/Ao | 0.01 | 0.25 | 0.14 | 0.01 |

TABLE 6-continued

| | Example 2-(1) | Comparative Example 2-(1) | | |
|---|---|---|---|---|
| variation (S.D.) | | | | |
| CRP content ($\bar{x}$) | 501 µg/ml | 7.5 | 5.4 | 3.2 |
| x variation (S.D.) | 0.40 | 2.10 | 1.02 | 0.29 |
| Coefficient of variation (C.V. %)* | 7.8 | 28 | 19 | 9.1 |

$*C.V.(\%) = \frac{S.D.}{\bar{x}} \times 100$

TABLE 7

| Material to be measured | | Stirring Period | Measured Value of Content ($\bar{x}$) | Coefficient of Variation (CV) |
|---|---|---|---|---|
| hCG | Example 2-(2) | 40 to 52 sec. (45 sec. on average) | 9.8 IU | 5.5 |
| | Comparative Example 2-(2) | 45 sec. | 10.5 | 11 |
| | | 300 sec. | 7.3 | 8.2 |
| AFP | Example 2-(3) | 28 to 35 sec. (32 sec. on average) | 47 µg/ml | 6.8 |
| | Comparative Example 2-(3) | 30 sec. | 56 | 14 |
| | | 300 sec. | 28 | 4.6 |
| $\beta_2$-microglobulin | Example 2-(4) | 32 to 41 sec. (35 sec. on average) | 5.1 µg/ml | 6.3 |
| | Comparative Example 2-(4) | 35 sec. | 5.1 | 17 |
| | | 300 sec. | 3.6 | 6.0 |

What we claim is:

1. A method for measuring an immunologically active material by optically measuring a degree of agglutination of a reaction mixture, which is produced by chemically immobilizing a material which is selectively immunologically active to a material in a specimen to be quantitated on dehydrated solid fine particles, and reacting in a liquid medium said specimen with said immobilized selectively immunologically active material, said method comprising the steps of:

(i) providing dry reagent fine particles comprising dehydrated solid fine particles ranging in size from 0.05 µm to 5 µm, the surfaces of said fine particles comprising a material which is selectively immunologically active to a material contained in a specimen to be quantitated, said material on said surfaces of said fine particles being chemically immobilized on said surfaces of said fine particles, (ii) placing said dry reagent fine particles and said specimen in a measuring cell and adding a dispersing medium into said measuring cell, (iii) stirring said dry reagent fine particles and said specimen and said dispersing medium to produce a mixture in a dispersed state in said measuring cell while optically measuring a degree of dispersion of said mixture comprising said dry regent fine particles and said dispersing medium and said specimen in said measuring cell and while confirming if the ratio of an index A obtained by the equation (1):A=logIo/I versus an index Ao obtained by the equation (2):Ao=logI'o/I' satisfies the equation: $A/Ao \leq 1.1$, wherein the equation (1) is of a dispersed body comprising said dry reagent fine particles dispersed in said dispersing medium, Io is a intensity of incident monochromatic light upon passing through said measuring cell containing said dispersed body, and I is an intensity of light transmitted or scattered when said monochromatic light is passed through said measuring cell, and wherein the equation (2) is of a reference standard dry reagent particles dispersed body, I'o is an intensity of incident monochromatic light upon passing through a measuring cell containing said reference standard dry reagent particles dispersed body, and I' is an intensity of light transmitted or scattered when said monochromatic light is passed through said measuring cell; and terminating the stirring when the equation: $A/Ao \leq 1.1$ is satisfied to obtain a desired dispersion in said measuring cell, (iv) reacting said dispersion containing said specimen and said immobilized material to produce agglutination, and (v) optically measuring the degree of the agglutination produced in step (iv).

2. The method according to claim 1, wherein the predetermined degree of dispersion is determined by preliminarily preparing optically measured data of the degree of dispersion of dry reagent fine particles in a dispersion medium, and comparing the data with the optically measured degree of dispersion obtained in step (iv).

3. The measuring method according to claim 1, wherein the material to be measured is CRP.

4. The measuring method according to claim 1, wherein the material to be measured is hCG.

5. The measuring method according to claim 1, wherein the material to be measured is α-fetoprotein.

6. The measuring method according to claim 1, wherein the material to be measured is $\beta_2$-microglobulin.

7. A method for measuring an immunologically active material by optically measuring a degree of agglutination of a reaction mixture, which is produced by chemically immobilizing a material which is selectively immunologically active to a material in a specimen to be quantitated on dehydrated solid fine particles, and reacting in a liquid medium said specimen with said immobilized selectively immunologically active material, said method comprises the steps of:

(i) providing dry reagent fine particles comprising dehydrated solid fine particles ranging in size from 0.05 μm to 5 μm, the surfaces of said fine particles comprising a material which is selectively immunologically active to a material contained in a specimen to be quantitated, said material on said surfaces of said fine particles being chemically immobilized on said surfaces of said fine particles, (ii) placing said dry reagent fine particles and said specimen into a reaction cell and adding a dispersing medium into said reaction cell;

(iii) stirring said dry reagent fine particles and said specimen and said dispersing medium to produce a mixture in a dispersed state in said reaction cell while optically measuring a degree of dispersion of said mixture comprising said dry reagent fine particles and said dispersing medium and said specimen in said reaction cell and while confirming if the ratio of an index A obtained by the equation (1): $A=\log Io/I$ versus an index Ao obtained by the equation (2): $Ao=\log I'o/I'$ satisfies the equation: $A/Ao \leq 1.1$, wherein the equation (1) is of a dispersed body comprising said dry reagent fine particles dispersed in said dispersing medium, Io is a intensity of incident monochromatic light upon passing through said reaction cell containing said dispersed body, and I is an intensity of light transmitted or scattered when said monochromatic light is passed through said reaction cell, and wherein the equation (2) is of a reference standard dry reagent particles dispersed body, I'o is an intensity of incident monochromatic light upon passing through a reaction cell containing said reference standard dry reagent particles dispersed body, and I' is an intensity of light transmitted or scattered when said monochromatic light is passed through said reaction cell and terminating the stirring when the equation: $A/Ao \leq 1.1$ is satisfied to obtain a desired dispersion in said reaction cell (iv) reacting said dispersion containing said specimen and said immobilized material to produce agglutination in said reaction cell, (v) flowing the reaction mixture caused in said reaction cell in step iv into a measuring cell, and (vi) optically measuring the degree of the agglutination of the reaction mixture in said measuring cell.

8. The method according to claim 1, wherein the predetermined degree of dispersion is determined by preliminarily preparing optically measured reference data of the degree of dispersion of dry reagent fine particles in a dispersion medium, and comparing the data with the optically measured degree of dispersion obtained in step (iv).

9. The measuring method according to claim 1, wherein the optical measurement of the agglutination state in the step (vi) is carried out under flow of a diluent after diluting the reaction mixture obtained in the step (v) with the diluent.

* * * * *

UNITED STATES PATENT AND TRADEMARK OFFICE
CERTIFICATE OF CORRECTION

PATENT NO. : 5,679,581

DATED : October 21, 1997

INVENTOR(S) : TAKESHI MIYAZAKI, ET AL.  Page 1 of 6

It is certified that error appears in the above-identified patent and that said Letters Patent is hereby corrected as shown below:

COLUMN 1

Line 17, "use-of" should read --use of--;
    Line 19, "relates" should read --relates to--;
    Line 46, "optically" should read --optical--;
    Line 52, "that" should read --in that--; and
    Line 53, "greately" should read --greatly--.

COLUMN 2

Line 6, "redisperse" should read --redispersing--;
    Line 25, "that" should read --in that--;
    Line 54, "whereby" should read --thereby--; and
    Line 67, "logically" should read --logical--.

COLUMN 3

Line 17, "stirring" should read --the stirring--;
    Line 22, "stirring" should read --the stirring--; and
    Line 54, "embodiment" should read --embodiments--.

COLUMN 4

Line 34, "dried:" should read --dried;--; and
    Line 35, "dispersion" should read --the dispersion--.

COLUMN 5

Line 17, "in" should read --into--;
    Line 37, "dry" should read --a dry--; and
    Line 61, "Staphylococcus sp., Streptococcus sp." should be italicized.

UNITED STATES PATENT AND TRADEMARK OFFICE
CERTIFICATE OF CORRECTION

PATENT NO. : 5,679,581

DATED : October 21, 1997

INVENTOR(S) : TAKESHI MIYAZAKI, ET AL.

It is certified that error appears in the above-identified patent and that said Letters Patent is hereby corrected as shown below:

COLUMN 6

Line 25, "Trypanosoma," should be italicized;
    Line 26, "Plasmodium," should be italicized; and
    Line 62, "glutalaldehyde," should read --glutaraldehyde,--.

COLUMN 7

Line 59, "there" should read --these--.

COLUMN 8

Line 16, "optically" should read --optical--.

COLUMN 9

Line 17, "of" should read --of the--;
    Line 18, "of" should read --of the--;
    Line 52, "drying" should read --the drying--; and
    Line 55, "o Ao" should read --Ao--.

COLUMN 10

Line 49, "preliminary" should read --preliminarily--;
    Line 51, "Experiment 2-(2)" should read
        --¶ Experiment 2-(2)--; and
    Line 55, "plymethylmethacrylate," should read
        --polymethylmethacrylate--.

COLUMN 12

Line 1, "preliminary" should read --preliminarily--;
    Line 30, "logically" should read --logical--;
    Line 62, "use" should read --to use--; and

UNITED STATES PATENT AND TRADEMARK OFFICE
CERTIFICATE OF CORRECTION

PATENT NO. : 5,679,581

DATED : October 21, 1997

INVENTOR(S) : TAKESHI MIYAZAKI, ET AL.

It is certified that error appears in the above-identified patent and that said Letters Patent is hereby corrected as shown below:

COLUMN 13

Line 8, "a" (first occurrence) should read --an--;
    Line 20, "is" should read --are--; and
    Line 27, "twice" should read --two--.

COLUMN 14

Line 23, "Beam" should read --A beam--;
    Line 28, "use" should read --to use--;
    Line 41, "a" (first occurrence) should read --an--;
    Line 53, "is" should read --are--; and
    Line 60, "curve." should read --curve was performed.--.

COLUMN 15

Line 7, "sent" should read --sent to--.

COLUMN 16

Line 31, "bibration" should read --vibration--; and
    Line 40, "is" should read --are--.

COLUMN 17

Line 8, "a" should read --an--;
    Line 19, "a" should read --an--;
    Line 26, "preliminary" should read --preliminarily--; and
    Line 42, "time)," should read --times),--.

UNITED STATES PATENT AND TRADEMARK OFFICE
CERTIFICATE OF CORRECTION

PATENT NO. : 5,679,581

DATED : October 21, 1997

INVENTOR(S) : TAKESHI MIYAZAKI, ET AL.

It is certified that error appears in the above-identified patent and that said Letters Patent is hereby corrected as shown below:

COLUMN 18

Line 22, "preliminary" should read --preliminarily--;
    Line 32, "result" should read --results--; and
    Line 63, "-microblobulin" should read
        -- -microglobulin--.

COLUMN 19

Line 2, "-miroglobulin." should read -- -microglobulin.--;
    Line 18, "preliminary" should read --preliminarily--; and
    Line 57, "The" should read --To--.

COLUMN 20

Line 38, "laser" should read --a laser--; and
    Line 65, "increase" should read --increases--.

COLUMN 21

Line 49, "preliminary" should read --preliminarily--;
    Line 56, "laser" should read --a laser--; and
    Line 60, "a" should read --an--.

COLUMN 22

Line 49, "preliminary" should read --preliminarily--;
    Line 50, "nm];" should read --nm;--; and
    Line 56, "laser" should read --a laser--.

UNITED STATES PATENT AND TRADEMARK OFFICE
CERTIFICATE OF CORRECTION

PATENT NO. : 5,679,581

DATED : October 21, 1997

INVENTOR(S) : TAKESHI MIYAZAKI, ET AL.

It is certified that error appears in the above-identified patent and that said Letters Patent is hereby corrected as shown below:

COLUMN 23

Line 40, "cell" should read --cell.--;
    Line 48, "nary" should read --narily--;
    Line 54, "laser" should read --a laser--; and
    Line 59, "a" should read --an--.

COLUMN 24

Table 2, "REPROPUCIBUTY" should read --REPRODUCIBILITY--; and
    Table 3, "CONCURENT REPROPUCIBUTY" should read --CONCURRENT REPRODUCIBILITY-- and "250 sec." should read --250 sec.)--.

COLUMN 25

Table 3-continued, "Nete" should read --Net--;
    Table 4, "CONCURENT REPROPUCIBUTY" should read --CONCURRENT REPRODUCIBILITY--;
    Table 5, "104 Δ" should read --104 x--; and
    Table 6, "sec. on average" should read --sec. on average)--.

COLUMN 27

Line 4, "a intensity" should read --an intensity--.

UNITED STATES PATENT AND TRADEMARK OFFICE
CERTIFICATE OF CORRECTION

PATENT NO. : 5,679,581

DATED : October 21, 1997

INVENTOR(S) : TAKESHI MIYAZAKI, ET AL.　　　　Page 6 of 6

It is certified that error appears in the above-identified patent and that said Letters Patent is hereby corrected as shown below:

COLUMN 28

```
Line 3, "cell;" should read --cell,--;
Line 17, "a" should read --an--; and
Line 31, "cell" should read --cell,--.
```

Signed and Sealed this

Second Day of June, 1998

Attest:

BRUCE LEHMAN

Attesting Officer　　　Commissioner of Patents and Trademarks